United States Patent [19]

Munderloh et al.

[11] Patent Number: 5,869,335
[45] Date of Patent: Feb. 9, 1999

[54] **METHOD OF GROWING RICKETTSIAE IN *IXODES SCAPULARIS* TICK CELL CULTURE AND PREPARING ANTIGENS AND VACCINES OF RICKETTSIAE**

[75] Inventors: Ulrike G. Munderloh; Timothy J. Kurtti, both of Falcon Heights, Minn.; Katherine M. Kocan, Stillwater, Okla.; Edmour F. Blouin, Stillwater, Okla.; Sidney A. Ewing, Stillwater, Okla.

[73] Assignee: Regents of the University of Minnesota, Minneapolis, Minn.

[21] Appl. No.: 519,599

[22] Filed: Aug. 25, 1995

[51] Int. Cl.$^6$ ..................................................... C12N 1/00
[52] U.S. Cl. ........................ 435/348; 435/374; 435/395; 435/400; 435/243; 435/248; 435/253.6; 435/260; 424/265.1
[58] Field of Search ........................ 424/265.1; 435/348, 435/374, 395, 400, 243, 248, 253.6, 260

[56] References Cited

U.S. PATENT DOCUMENTS

| | | | |
|---|---|---|---|
| 3,505,456 | 4/1970 | Barrett . | |
| 3,511,908 | 5/1970 | Brock et al. . | |
| 3,616,202 | 10/1971 | Marble | 195/1.8 |
| 3,674,860 | 7/1972 | Welter et al. | 424/88 |
| 4,307,191 | 12/1981 | Ristic et al. | 435/32 |
| 4,447,537 | 5/1984 | Yunker et al. . | |
| 4,956,278 | 9/1990 | Hart et al. | 435/30 |

FOREIGN PATENT DOCUMENTS

| | | |
|---|---|---|
| 0 196 290 A2 | 10/1986 | European Pat. Off. . |
| WO 83/00017 | 1/1983 | WIPO . |
| WO 90/12030 | 10/1990 | WIPO . |

OTHER PUBLICATIONS

Munderloh et al., 1996 (Jul.) *Journal Medical Entomology*, 33:656–664 "Establishment of the tick, etc.".
Hidalgo, et al., 1989 (Dec.), *Am. J. Vet. Res.* 50:2028–2032 "*Anaplasma marginale* in tick cell culture".
Munderloh, et al., 1989, *Experimental & Applied Acarology* 7:219–229 "Formulation of medium for tick cell culture".
Brouqui et al., 1992 (May), *Journal Clinical Microbiology* 30:1062–1066 "Antigenic characterization of Ehrlichiae: etc.".
Wheeler et al., 1991 (Dec.) *Journal of Parasitology* 77:965–973 "Salivary gland antigens of *Ixodes dammini*, etc.".
Palmer, et al., 1986 (Mar.), *Science* 231:1299–1302 "Immunization with an isolate–common surface protein protects cattle against anaplasmosis".
Vidotto, et al., 1994 (Jul.), *Infection and Immunity* 62:2940–2946 "Intermolecular relationships of major surface proteins of *Anaplasma marginale*".
Amerault et al, "A Rapid Card Agglutination Test for Bovine Anaplasmosis", *J. Am. Vet. Med. Assoc.* 153:1828–1834 (Dec. 15, 1968).
Ascher et al, "Initial Clinical Evaluation of a New Rocky Mountain Spotted Fever Vaccine of Tissue Culture Origin", *J. Infect. Dis.* 138:217–221 (Jul. 1978).

Barbet et al, "The msp1β Multigene Family of *Anaplasma marginale*. Nucleotide Sequence Analysis of an Expressed Copy", *Inf. Immun.* 59:971–976 (Mar. 1991).
Breed et al, "Tribe II. Ehrlichieae Philip, Trib. Nov." In: *Bergey's Manual of Determinative Bacteriology*, pp. 948–952, The Williams & Wilkins Company (ed.), Baltimore, MD (1957).
Chen et al, "Identification of a Granulocytotropic Ehrlichia Species as the Etiologic Agent of Human Disease", *J. Clin. Microbiol.* 32: 589–595 (Mar., 1994).
Chen et al, "Cytogenetic Characteristics of Cell Lines from Ixodes scapularis (Acari: Ixodidae)", *J. Med. Entom.* 31:425–434 (1994).
Coan et al, "Persistence of *Anaplasma marginale* infectivity and tick," *Proceedings of the 8th National Veterinary Hemoparasite Diseases Congress*, St. Louis, MO (1989), pp. 161–176.
Coan et al, *9th Annual Western Conference for Food Animal Disease Research*, p. 34 (Apr. 1988) (Abstract), "Tick survival and intrastadial persistence of *Anaplasma marginale* in a male ixodid vector held in modified natural surroundings".
Coan et al, (Abstract) 70th Am. Pac. Branch Meeting of the Entomological Society of America, San Diego, CA, p. 66 (1986).
Dawson et al, "Isolation and Characterization of an Ehrlichia sp. from a Patient Diagnosed with Human Ehrlichiosis", *J. Clin. Microbiol.* 29:2741–2745 (Dec. 1991).
Dikmans, G., "The Transmission of Anaplasmosis", *Am. J. Vet. Res.* 38:5 (Jan., 1950).
Ewing, S.A., "Transmission of *Anaplasma marginale* by Arthropods," pp. 395–423.
Ewing, S.A., "Ehrlichia Canis in Tick Cell Culture," 76th Conference of Research Workers in Animal Diseases (Abstract).
Ge et al, "Detection of *Anaplasma marginale* DNA in bovine erythrocytes by slot–blot and in situ hybridization with a PCR–mediated digoxigenin–labeled DNA probe", *J. Vet. Diagn Invest.* 7:465–472 (1995).

(List continued on next page.)

*Primary Examiner*—James C. Housel
*Assistant Examiner*—Jennifer Shaver
*Attorney, Agent, or Firm*—Merchant, Gould, Smith, Edell & Welter

[57] ABSTRACT

The invention is directed to methods of culturing rickettsiae in *Ixodes scapularis* cell lines. The methods of the invention provide for culture of microorganisms such as *Anaplasma marginale*, *Ehrlichia canis*, and *Rickettsia rickettsii*. A method of the invention involves incubating a rickettsia with an *Ixodes scapularis* tick cell culture in a culture medium under reduced oxygen and increased $CO_2$ at a sufficient temperature until growth of the rickettsia is detected. The culture medium comprises a medium suitable for the growth of invertebrate cells supplemented with an organic buffer. The cell culture method can be used in large scale production of rickettsia containing products useful in diagnostic assays and vaccine preparations.

17 Claims, 14 Drawing Sheets

OTHER PUBLICATIONS

Goff et al, "Comparison of a DNA probe, complement–fixation and indirect immunofluorescene tests for diagnosing *Anaplasma marginale* in suspected carrier cattle", *Vet. Microbiol.* 24:381–390 (1990).

Higuchi, "Simple and Rapid Preparation of Samples for PCR", In: *PCR Technology, Principles and Applications for DNA Applications,* pp. 31–38, H.A. Erlich (ed.), Stockton Press, NY (1989).

Kocan, et al., "Development of *Anaplasma marginale* in male *Dermacentor andersoni* transferred from parasitemic to susceptible cattle", *Am. J. Vet. Res.* 53: 499–507 (Apr. 1992).

Kocan et al, "Persistence of *Anaplasma marginale* (Rickettsiales: Anaplasmataceae) in Male *Dermacentor andersoni* (Acari: Ixodidae) Transferred Successively from Infected to Susceptible Calves", *J. Med. Ent.* 29:657–668 (Jul. 1992).

Kocan, K., "Anaplasmosis in Oklahoma and the South Central United States", Proc. U.S. Animal Health Assoc. Mtg., Oct. 30–Nov. 4 (1994).

Kurtti et al, "The Interaction of *Babesia caballi* Kinetes with Tick Cells", *J. Invert. Path.* 42:334–343 (Jul., 1983).

Kurtti et al, "In Vitro Developmental Biology and Spore Production in *Nosema fumacalis* (Microspora: Nosematidae)", *J. Invert. Path.* 63:188–196, Mar. (1994).

Kurtti et al, "Ultrastructural analysis of the invasion of tick cells by Lyme disease spirochetes (*Borrelia burgdorferi*) in vitro", *Can. J. Zool.* 72:977–994, Jun. (1994).

Kurtti et al, "Adhesion to and Invasion of Cultured Tick (Acarina: Ixodidae) Cells by *Borrelia burgdorferi* (Spirochaetales: Spirochaetaceae) and Maintenance of Infectivity", *J. Med. Entom.* 30:586–596 (1993).

Laemmli, U.K., Nature 227:680–685 (1970).

Leibovitz, A., "The Growth and Maintenance of Tissue–Cell Cultures in Free Gas Exchange with the Atmosphere", *Am. J. Hyg.* 78:173–180 (1963).

Maeda, et al., "Human Infection with Ehrlichia Canis, a Leukocytic Rickettsia", *New Eng. J. Med.* 316:853–856 (Apr. 2, 1987).

McCallon, B.R., "Prevalence and Economic Aspects of Anaplasmosis", *Proceedings of the 6th National Anaplasma Conference,* Heritage Press, Stillwater, OK (1973).

McGarey, et al., "Putative Adhesins of *Anaplasma marginale*: Major Surface Polypeptides 1a and 1b", *Inf. Immun.* 62:4594–4601, Oct. (1994).

McGuire et al, "Common and Isolate–Restricted Antigens of Anaplasma marginale Detected with Monoclonal Antibodies", *Inf. Immun.* 45(3):697–700 (1984).

Montenegro et al, "Utilization of Culture–Derived Soluble Antigen in the Latex Agglutination Test for Bovine Babesiosis and Anaplasmosis", *Vet. Paras.* 8:291–297 (1981).

Munderloh et al, "Cellular and Molecular Interrelationships Between Ticks and Prokaryotic Tick–Borne Pathogens", *Annu. Rev. Entomol.* 40:221–243, Jan. (1995).

Munderloh et al, "Plasmid modifications in a tick–borne pathogen, *Borrelia burgdorferi*, cocultured with tick cells", *Insect Mol. Biol.* 1(4):195–203 (1993).

Munderloh et al, "Formulation of Medium for Tick Cell Culture", *Exper. Appl. Acarology* 7:219–229 (1989).

Munderloh et al, "Establishment, Maintenance and Description of Cell Lines From the Tick Ixodes Scapularis", *J. Parasitol.* 80:533–543, Aug. (1994).

Nichols et al, "Cytogenetic Studies on Cells in Culture from the Class Insecta," In: *Current Topics in Microbiology amd Immunology,* pp. 61–69, Arber et al (ed), Springer–Verlag New York, Heidelberg, Berlin (1971).

Oliver et al, "Conspecificity of the Ticks Ixodes scapularis and I. dammini (Acari: Ixodidae)", *J. Med. Entom.* 30:54–63 (1993).

Palmer, G.H., "Anaplasma Vaccines, " In: *Veterinary Protozoan and Hemoparasite Vaccines,* pp. 2–29, I.G. Wright (ed), CRC Press (1989).

Pasteur et al, "Standard Solutions for Electrophoresis and Staining," In: *Practical Isozyme Genetics,* pp. 93–94, 134–137, Ellis Horwood Limited, Chichester, UK, West Sussex (1988).

Rikihisa, Y., "The Tribe Ehrlichieae and Ehrlichial Disease", *Clin. Microbiol. Rev.* 4:286–308 (1991).

Ristic, M., "A Capillary Tube–Agglutination Test for Anaplasmosis–A Preliminary Report", *J. Am. Vet. Assoc.* 141:588–594 (1962).

Ristic et al, "An Overview of Research on Ehrlichiosis", *Eur. J. Epidemiol.* 7(3):246–252 (1991).

Rodgers et al, "A serological survey of *Ehrlichia canis, Ehrlichia equi, Rickettsia rickettsii,* and *Borrelia burgdorferi* in dogs in Oklahoma", *J. Vet. Diagn. Invest.* 1:154–159 (1989).

Samish, et al, "Cultivation of *Anaplasma marginale* from cattle in a Dermacentor cell line", *Am. J. Vet. Res.* 49:254–256 (Feb., 1988).

Schuntner et al, "Radiommunoassay for *Anaplasma marginale* antibodies in cattle", *Am. J. Vet. Res.* 49:504–507 (1988).

Shkap et al., "An enzyme–linked immunosorbent assay (ELISA) for the detection of antibodies to *Anaplasma centrale* and *Anaplasma marginale",* Vet. Microbiol. 25:45 (1990).

Slovut, G, "Six New Cases of Dangerous Tick–Borne Disease Found Near Duluth,"*Mpls. Star & Tribune,* Jul. 13, 1995.

Stich et al, "Detection of *Anaplasma marginale* (Rickettsiales: Anaplasmataceae) in Hemolymph of *Dermacentor andersoni* (Acari: Ixodidae) with the Polymerase Chain Reaction", *J. Med. Entomo.* 30:781–788 (Jul. 1993).

Vidotto et al, "Intermolecular Relationships of Major Surface Proteins of *Anaplasma marginale", Inf. Immun.* 62:2940–2946, Jul. (1994).

Wysoki et al, "Spermatogenesis, Chromosomes and Sex Determination of four Rhipicephalus Species (ACARI: Ixodidae) From East Africa", *Genetica* 48(3):233–238 (1978).

Yunker, C.E., "Preparation and Maintenance of Arthropod Cell Cultures: Acari, with Emphasis on Ticks," In: *Arboviruses in Arthropod Cells In Vitro,* pp. 37–51 (1987).

*A Microtiter Technique for Complement Fixation Text for Anaplasmosis,* Manual, USDA Animal and Plant Health Inspection Service, Beltsville, MD, pp. 1–16 (1968).

*Sambrook et al., *A Guide to Molecular Cloning: A Laboratory Manual,* Cold Spring Harbor Laboratory (1989).

FIG. IA
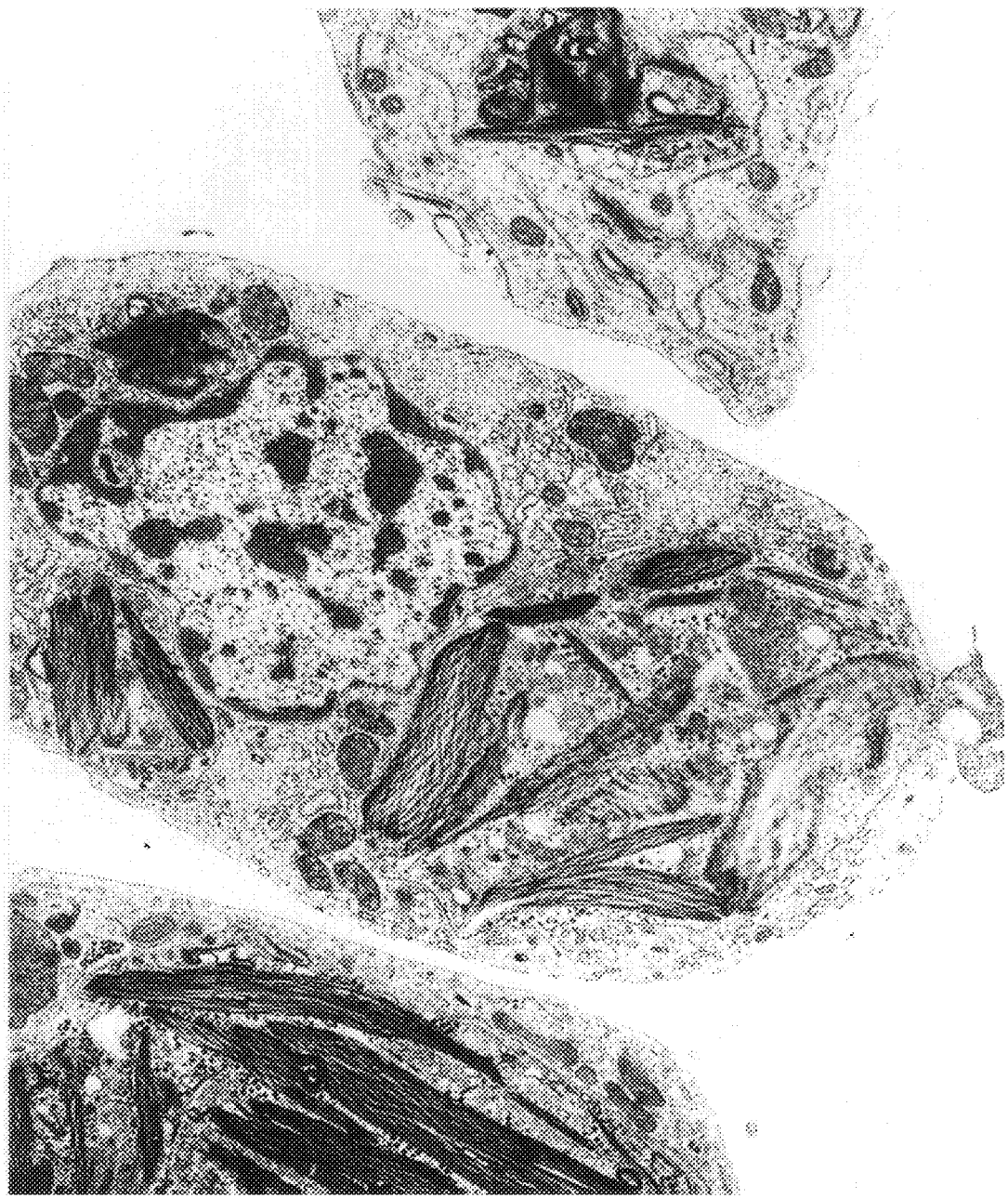

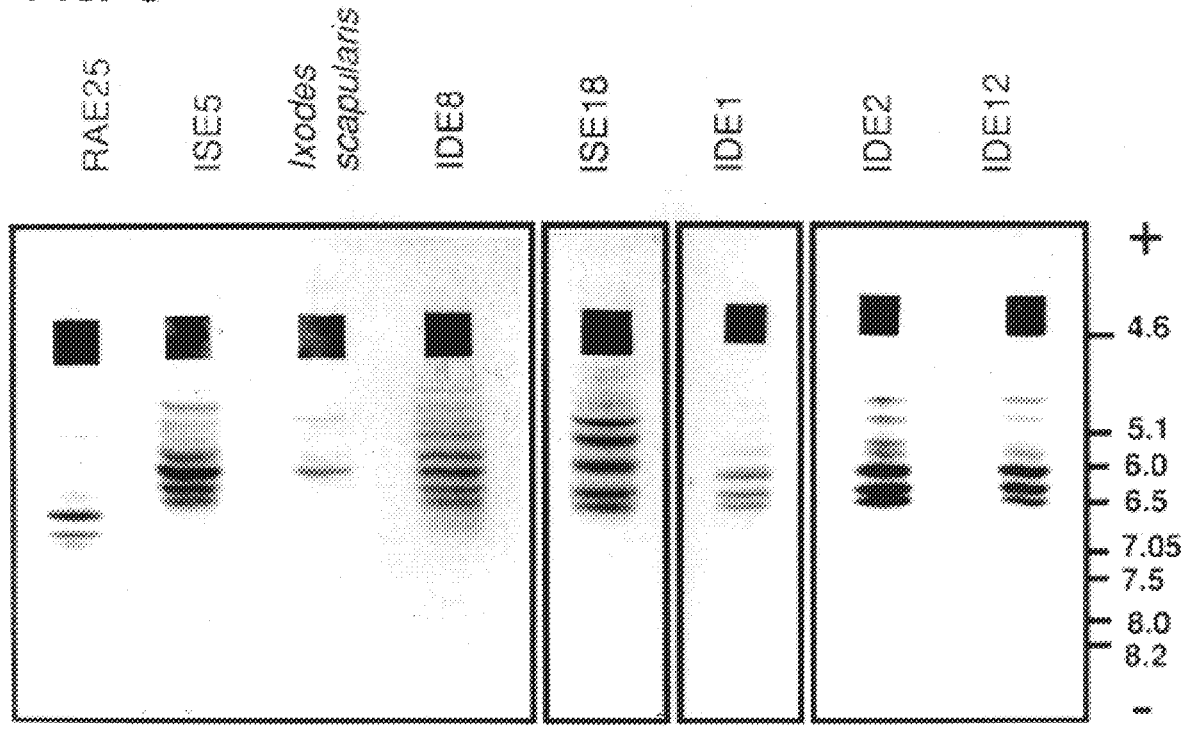

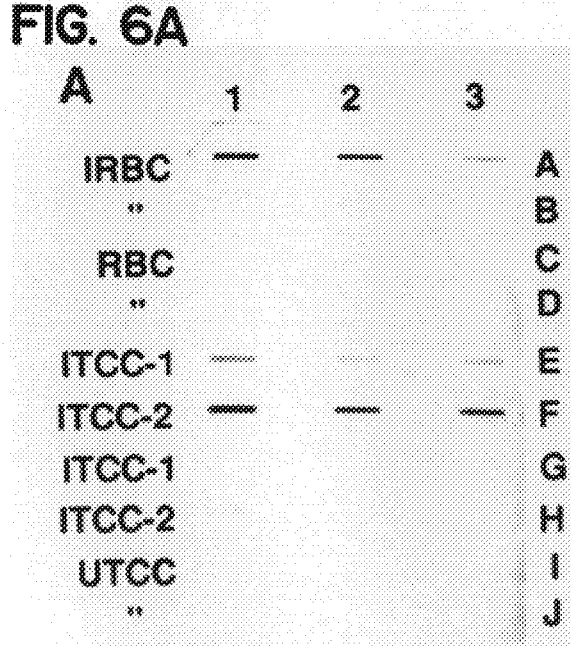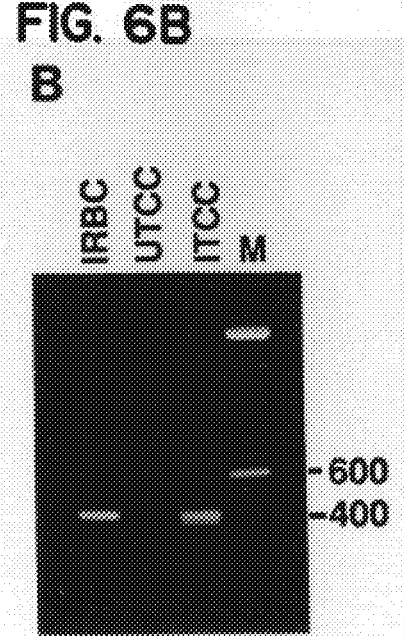
FIG. 6A
FIG. 6B

FIG. IIA
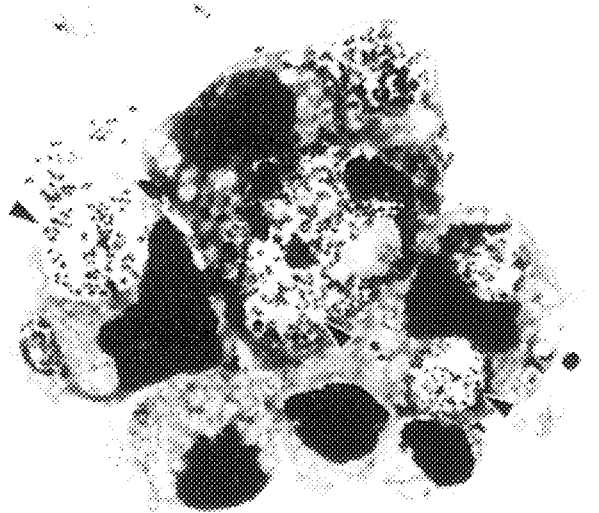
FIG. IIB
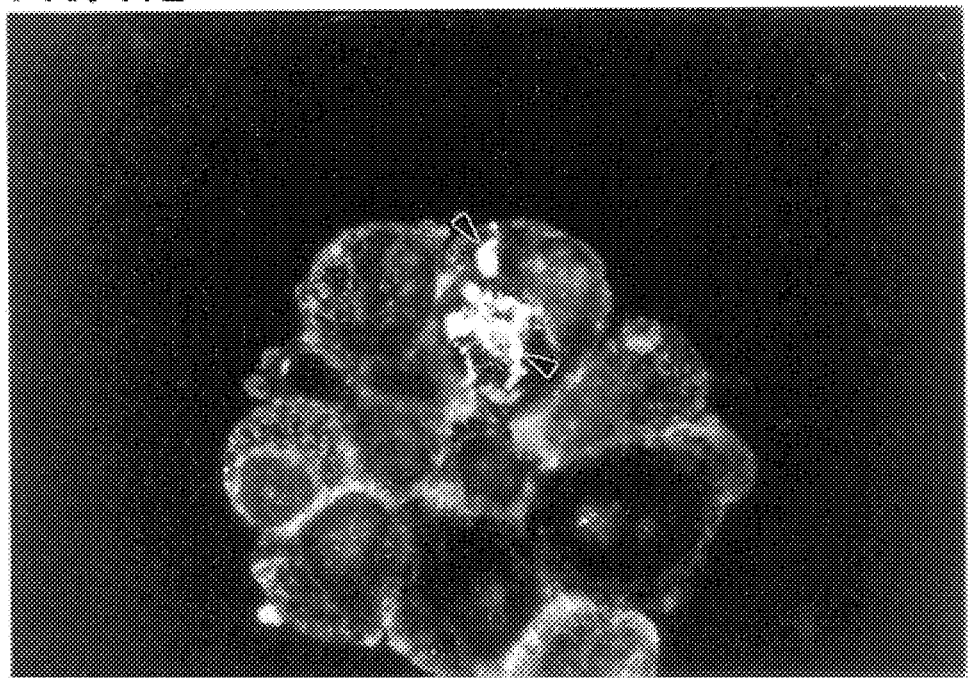

METHOD OF GROWING RICKETTSIAE IN *IXODES SCAPULARIS* TICK CELL CULTURE AND PREPARING ANTIGENS AND VACCINES OF RICKETTSIAE

The work described herein was supported in part with funds from the Minnesota Agricultural Experiment Station (project 377–3457), the Oklahoma Agricultural Experiment Station (projects 1669 and 1433), and grants from the USDA/NRI Competitive Grants Program, No. 94-37204-0449, 91-37204-6360, and Grant No. AR37909 from the National Institutes of Health. The government may have certain rights in the invention.

BACKGROUND OF THE INVENTION

Rickettsiae with the exception of Rochalimaea are obligate intracellular parasites. As such, these microorganisms are often difficult to grow and the diseases they cause are difficult to diagnose. Because of the difficulty of growing these microorganisms, large scale preparation of vaccines and antigens has been costly and sometimes impossible. Many of the rickettsiae are the pathogenic agents of vector-transmitted diseases of human and animals. They are transmitted by invertebrate vectors such as ticks. Within rickettsiae, the microorganisms of the Anaplasma, Ehrlichia and Rickettsia genera are the causative agents of vector transmitted diseases and are difficult to grow, especially on a large scale.

Anaplasmosis is the only major tick-borne disease of cattle endemic in the United States. The causative agent, *Anaplasma marginale*, invades and multiplies in erythrocytes of cattle causing mild to severe anemia. Annual mortality and morbidity due to anaplasmosis among U.S. beef cattle has been estimated at 50,000 to 100,000 head and a cost of $300 million. The average weight loss during acute infections is 86 kg, with increased veterinary costs estimated at $52/head (Palmer in Veterinary Protozoan and Hemoparasite Vaccines, J. G. Wright (Ed.) CRC Press Inc., Boca Raton, Fla. 1989). The resultant loss of cattle for the export market has been estimated at $45 million annually (McCallon 1973).

Anaplasmosis can be transmitted biologically by several species of hard ticks (Dikmans Amer. J. Vet. Res. 38:5 (1950); Ewing, S. Transmission of *Anaplasma marginale* in Arthropods in Proc: 7th National Anaplasmosis Conference, Mississippi State MS p 395, 1981) or mechanically by blood-contaminated mouthparts of biting flies or fomites. In some geographical areas, transmission has been thought to occur primarily by biting flies and thus, the disease has been called “fly fever”. However, ticks most likely play a major role in transmission of this disease. Male ticks are believed to contribute markedly to transmission of *A. marginale*. (Coan and Stiller, Abst. 70th Am. Pacific Branch Mtg. of Entomological Soc. Amer., Sand Diego, Calif. p.66 (1986); Coan et al., Ann. Western Conf. of Food Ani. Vet. Med., Boise, ID p.34 (1987); Coan et al., Proc. 8th National Vet. Hemoparasit. Dis. Conference, St. Louis, Mo. pp. 1161 (1989); Kocan et al., Am. J. Vet. Res. 53:499 (1992a); Kocan et al., J. Med. Entomol. 29:657 (1992b)). Male ticks can acquire infection as adults by feeding for short periods on infected cattle. Because male ticks are intermittent feeders, they readily detach and can reattach to other cattle during their life. Interhost transfer of male Dermacentor ticks among cattle has been clearly demonstrated. These male ticks have been shown to be persistently infected with *A. marginale* and are able to transmit the rickettsia repeatedly to susceptible cattle (Kocan et al. 1992b cited supra).

The widening distribution of anaplasmosis is probably contributed to by increased movement of cattle and the lack of sensitivity of the complement-fixation test. The complement-fixation test for anaplasmosis has been shown to lack sensitivity, especially in calves, carrier cattle and in cattle that have been treated with tetracyclines which lowers antibody titers often to undetectable levels (Goff et al., Vet. Microbiol. 24:381 (1990)). Thus, cattle may be shipped as serologically negative when they actually are active carriers of the organism. These carrier cattle are then likely to serve as reservoirs of infection for mechanical transmission by blood-contaminated fomites, biting flies or biologically by ticks.

Serologic diagnosis of anaplasmosis is predominantly accomplished by the complement-fixation test (USDA, A microtiter technique for complement fixation text for anaplasmosis, Manual pp. 1–16, USDA Animal and Plant Health Inspection Service, Beltsville, Md. (1968)). Many other tests have been developed to measure Anaplasma-specific antibodies, including the capillary-tube agglutination test (Ristic, J. Am. Vet. Assoc. 141:588 (1962)), card test (Amerault & Roby, J. Am. Vet. Assoc. 153:1828 (1968)), latex agglutination (Montenegro-James et al., Vet. Parasitology 8:241 (1981)), indirect fluorescent antibody test (IFAT) (Goff et al. 1990, cited supra), conventional ELISA (Shkap et al., Vet. Microb. 25:45 (1990)) and radioimmunoassay (Schunter & Leatch, Am. J. Vet. Res. 49:504 (1988)). Growth of *A. marginale* in cell culture may provide an inexpensive and more consistent antigen for use in serologic tests.

Control strategies for anaplasmosis in Oklahoma and elsewhere varies owing to the complexity of the disease and mode of transmission, and may include vector control, administration of tetracyclines, vaccination and maintenance of uninfected cattle. Current vaccines marketed in the U.S. are killed vaccines made from infected bovine blood. These vaccines reduce clinical symptoms but do not prevent infection. Vaccinated cattle that are challenge-exposed thereafter become carriers and their blood can serve as an infective source for ticks and/or mechanical transmission via biting flies and blood-contaminated instruments. Subunit vaccines which have been described provide only partial protection against challenge (Vidotto et al., Inf. and Imm. 62:2940 (1994)). In addition, many vaccine preparations can be contaminated with bovine red blood cell antigens as well as with other bovine pathogens.

Numerous attempts to grow *A. marginale* in a variety of mammalian and invertebrate cells have failed. Attempts included cell lines from *D. variabilis* ticks but none resulted in a continuous culture system capable of producing cattle-infective rickettsiae. *A. marginale* apparently does not invade nucleated cells in its vertebrate host, only erythrocytes. In contrast, the parasite develops in several types of nucleated tick cells (in midgut, gut muscle and salivary glands).

Erlichieae are rickettsial pathogens closely related to Anaplasma. Those species for which a biological vector is known are transmitted by ticks. While Anaplasma is confined to red cells in its mammalian host, the tick-borne Ehrlichieae infect white blood cells. Typically, Anaplasma and Ehrlichia are contained within membrane-bound vacuoles of their respective host cells.

The monocytic Ehrlichia species include *Ehrlichia canis* of dogs and *Ehrlichia chaffeensis, E. risticii* and *E. sennetsu*. These microorganisms are genetically related and cross-react serologically. The first Ehrlichia species recognized was *E. canis*. It occurs in all areas of the world where the vector tick, *Rhipicephalus sanguineus* (the brown dog tick), lives. The disease it causes is sometimes called canine tropical pancytopenia. It is a problem especially in all warm areas of the world, e.g., the southern U.S., Central and South America, the Mediterranean, South Asia (Ristic, M. and Huxsoll, D. L., 1984); Tribe II. Ehrlichieae Philip 1957. In: Bergey's manual of Systematic Bacteriology; Vol. 1, section 9). *Ehrlichia canis* can be cultivated in the dog cell line DH82 as well as human-dog hybrid cell lines (See: Rikihisa, Y. 1991. Clinical Microbiology Reviews, 4:286). *Ehrlichia chaffeensis* has been recognized only recently, and is associated with human ehrlichiosis. Maeda, K. et al., 1987, N. Eng. J. Med. 316:853; Dawson, J. E. et al., 1991, J. Clin. Microbiol. 29:2741). *E. chaffeensis* can also be cultured in DH82 cells. *E. risticii* is the causative agent of Potomac horse fever. This disease is known to occur in North America, France and India. *E. risticii* can be grown in macrophage-monocyte cell lines such as $P388D_1$, T-84 and U937. *E. sennetsu* is the causative agent of *Sennetsu erlichiosis* of humans. *E. sennetsu* grows in mice and cell lines such $P388D_1$ cells, L929 cells, and Hela cells.

Infections with monocytic Ehrlichiae can be diagnosed by direct microscopic examination and/or serodiagnosis. Treatment with antibiotics is effective. Two vaccines prepared from inactivated cell cultured *E. risticii* are commercially available for Potomac Horse Fever but none have been developed for large scale prevention of other ehrlichial diseases.

*Rickettsia rickettsii* is the causative agent of Rocky Mountain spotted fever. In the western U.S., the main vector of this human pathogen is the Rocky Mountain wood tick, *Dermacentor andersoni*. A close relative, *Dermacentor variabilis* also known as the American dog tick or common wood tick, is responsible for transmission in the eastern parts of the country. The disease is characterized by an acute febrile phase, typically with a disseminated rash. Unlike Anaplasma and Ehrlichia, which are passed only transstadially in ticks (from larvae to nymphs and/or nymphs to adults), *R. rickettsii* is transmitted transovarially and transstadially in the vector. After entry into the host cell, spotted fever rickettsiae do not remain in the phagosome, but quickly escape into the host cytoplasm, and commonly invade the nucleus. Their ability to move quickly from cell to cell by making use of the host cell's cytoskeletal elements is a characteristic feature leading to early dissemination to multiple tissues.

Vaccines against Rocky Mountain spotted fever were produced from inactivated organisms grown in embryonated hen's eggs, and more recently, in mammalian cell cultures. These vaccines are capable of preventing clinical illness, but not necessarily infection. Broad spectrum antibiotics, particularly chloramphenicol and tetracyclines, are highly effective when used promptly.

Thus there is a need to develop a culture system for growing rickettsiae in tick cell culture for use in diagnostics, and preparation of antigens and vaccines. There is a need to develop vaccines and antigen preparations that effectively protect against infection with *Anaplasma marginale* but that are not contaminated with bovine red blood cells or bovine pathogens. There is a need to develop a large scale culture system for preparation of large amounts of antigen from rickettsiae such as *Anaplasma marginale* and *Ehrlichia canis* for use in diagnostics and vaccines.

SUMMARY OF THE INVENTION

This invention is directed to methods of growing or culturing rickettsiae in *Ixodes scapularis* cell culture. The invention also includes rickettsial products produced by growing rickettsiae in tick cell culture.

A method of the invention includes culturing rickettsia with an *Ixodes scapularis* cell line in a culture medium under reduced oxygen and increased $CO_2$ at a sufficient temperature until growth of the rickettsia is detected. The culture medium comprises a medium suitable for the growth of invertebrate cells supplemented with an organic buffer. Preferably the cultures are incubated at a $CO_2$ level of about 3 to 5% at a temperature of about 31° C. to 35° C. The organic buffer is preferably present at a concentration of about 10 to 15 mM. Concentrations of organic buffer of 25 mM or more are toxic to the invertebrate cells. The preferred cells are *Ixodes scapularis* cell lines IDE8 or ISE6.

The cells are incubated until growth of rickettsia is detected. Growth can be detected by light microscopy, electron microscopy, fluorescent antibody staining, polymerase chain reaction, and hybridization with a probe specific for the particular rickettsial organism. For establishment of initial infection, the incubation period can be about 2 to 7 weeks. Once the microorganism is grown in the tick cells, it can be passaged by mixing infected cells with uninfected tick cells. Infected tick cell cultures are useful as diagnostic tools for serodiagnoses.

A method of the invention involves culturing of isolates of *A. marginale* with an *Ixodes scapularis* cell culture. *A. marginale* isolates can be obtained from blood from infected cattle. The *A. marginale* is incubated in a medium supplemented with about 10 to 15 mM MOPS and with a source of $HCO_3^-$. Preferably, the cells are incubated with about 0.25% $NaHCO_3$. The cells are incubated at about 34° to 35° C. until growth of *A. marginale* is detected. Growth of *A. marginale* can be detected using light microscopic methods, fluorescent antibodies, polymerase chain reaction and hybridization with an *A. marginale* specific probe.

The method of growing *A. marginale* is useful to produce *A. marginale* on a large scale at a lower cost. *A. marginale* grown in tick cell culture is useful to produce antigen and vaccine preparations. The antigen and vaccine preparations are essentially free of bovine red blood cell antigens and other bovine pathogens. The antigen and vaccine preparations can also contain tick cell antigens. The tick cells antigens may provide an additional protective effect.

A method of the invention is also directed to culturing monocytic Ehrlichia such as *E. canis*. *E. canis* can be incubated with an *Ixodes scapularis* tick cell culture in culture medium supplemented with an organic buffer and a source of $HCO_{3-}$. The *E. canis* is incubated with the tick cells under conditions of reduced oxygen and enhanced $CO_2$. Preferably, the cultures are incubated at about 17% oxygen and about 3 to 5% $CO_2$ at about 34° to 35° C. The tick cell cultures are incubated until growth of *E. canis* is detected. *E. canis*-infected tick cell cultures can be used as diagnostic tools for serodiagnosis. *E. canis* antigen preparations can also be prepared from *E. canis*-infected tick cell culture. The antigen preparations are essentially free of dog antigens and pathogens.

A method of the invention also provides for growth of Rickettsia such as *R. rickettsii*. *R. rickettsii* from infected ticks is incubated with an *Ixodes scapularis* cell line in a culture medium supplemented with an organic buffer. The infected cells can be incubated under normal atmospheric conditions. Optionally, the cells can be incubated with reduced oxygen and enhanced $CO_2$. Growth of rickettsiae in tick cells provides for large scale production of infected tick cultures and antigen preparations.

BRIEF DESCRIPTION OF THE FIGURES

FIG. 1. FIG. 1A is an electron micrograph of *Ixodes scapularis* tick cell line IDE8 at passage 17.

FIG. 5. Isoelectric focusing pattern of malic enzyme (ME) in *Ixodes scapularis* cell lines and tissue extracts from *I. scapularis* females compared with cell line RAE25 isolated from the tick *Rhipicephalus appendiculatus*. Samples in different panels were run in different gels. The pI values of standard enzymes are indicated on the margin of the right-hand panel. +, position of the anode and −, position of the cathode.

FIG. 6. Identity of *Anaplasma marginale* strain Am291 from tick cell culture. Panel 6A represents a slot blot hybridized with an *A. marginale*-specific, digoxigenin-labeled DNA probe. Lanes 1, 2, and 3 were loaded with 2-fold serial dilutions of the samples indicated on the left margin. IRBC, A and B: *A. marginale*-infected bovine red blood cells, positive control; RBC, C and D: uninfected bovine red blood cells, negative control; ITCC-1, E and G: infected tick cells from culture No. 1 (Am291 passage 2 in IDE8, 57% infected; ITCC-2, F and H: infected tick cells from culture No. 2 (Am291 passage 2 in IDE8, 61% infected); UTCC, I and J: uninfected tick cells, host cell control. Panel 6B represents an ethidium bromide-stained gel of a 409-bp DNA fragment of the msp-1βgene of *A. marginale* amplified by the polymerase chain reaction as described. Lysates were prepared from *A. marginale*-infected bovine red blood cells (IRBC, 56% parasitemia), and from infected (ITCC; Am291 passage 9 in IDE8 cells, over 90% infected) and uninfected IDE8 cells (UTCC) as described; M: 100 bp DNA ladder.

FIG. 11. Appearance of *Ehrlichia canis* in IDE8 tick cell culture. Top panel: Giemsa-stained smear of the first passage of *E. canis* in IDE8 cells. At the time the culture was sampled, approximately 67% of the cells were infected. Note the highly pleomorphic nature of individual organisms, and the large endosome containing many rickettsiae (arrows). Bottom panel: Immunofluorescent staining of *E. canis* in IDE8 cells, first passage in vitro. At the time the culture was sampled approximately 10% of the cells were infected. Arrows indicate ehrlichial inclusions.

DETAILED DESCRIPTION OF THE INVENTION

Figure 1B:
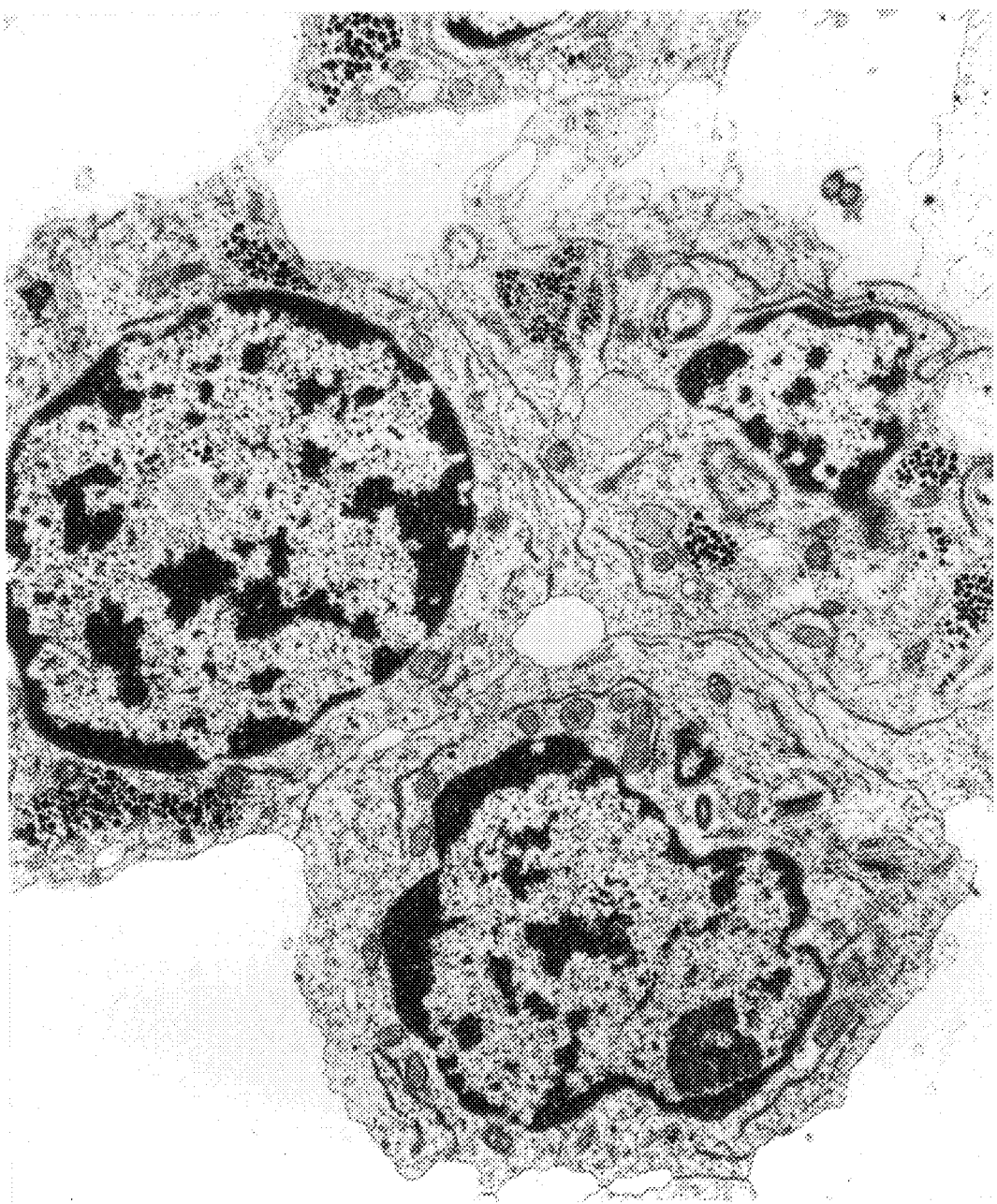
FIG. 1B is an electron micrograph of *Ixodes scapularis* tick cell line ISE6 at passage 10.

This invention is directed to methods of culturing rickettsiae in *Ixodes scapularis* tick cell cultures. Many members of rickettsiae have been difficult to culture in vitro, especially on a large scale. A method of growing rickettsiae in vitro is useful to prepare diagnostic tools, antigen preparations, and vaccine preparations. A method of the invention is useful to grow and/or culture rickettsiae on a large scale, resulting in production of rickettsial containing products at a high yield and a much reduced cost. In addition, large scale in vitro culture eliminates the need to maintain and/or euthanitize rickettsia-infected animals such as cattle which can cost about $2400 per animal. An in vitro culture method in *Ixodes scapularis* cell culture is also advantageous because rickettsial products can be obtained that are essentially free of contamination with mammalian antigens and/or other pathogens. In addition, rickettsial products can be obtained that include tick cell antigens which may be advantageous in stimulating a protective immune response.

The invention includes methods for culturing isolates of *Anaplasma marginale* in *Ixodes scapularis* tick cell culture. *Anaplasma marginale* is cultured under conditions of enhanced $CO_2$ and in a culture medium including an organic buffer. *Anaplasma marginale* grows in *Ixodes scapularis* cell culture at a high yield compared to growth in bovine erythrocytes. The invention is also directed to vaccine preparations and antigen preparations obtained from the tick cell culture. The vaccine and antigen preparations are essentially free of bovine antigens and other bovine pathogens. The invention is also directed to infected tick cell cultures which are useful as diagnostic tools.

The invention includes a method of culturing monocytic Ehrlichia such as *E. canis* in *Ixodes scapularis* tick cell culture. *E. canis* is cultured and grown under conditions of reduced oxygen and increased $CO_2$ in a medium supplemented with an organic buffer. *E. canis* grows in *Ixodes scapularis* cell culture at a high yield. The invention is also directed to antigen preparations of *E. canis* grown in *Ixodes scapularis* tick cell culture. The antigen preparations are essentially free of dog antigens and/or other dog pathogens. The invention is also directed to infected tick cell cultures which are useful as diagnostic tools.

The invention is also directed to a method for growing or culturing Rickettsia such as *R. rickettsii* in *Ixodes scapularis* tick cell culture. *R. rickettsii* grows to a high yield in *Ixodes scapularis* tick cells. The invention also includes vaccine preparations, antigen preparations and infected tick cell cultures.

*Ixodes scapularis* Tick Cell Culture

*Ixodes scapularis* tick cell cultures are prepared from embryonic tissues from the tick *Ixodes scapularis*. *Ixodes scapularis* tick cell cultures can be prepared using standard methods as described in Example 1. The *Ixodes scapularis* tick is not a natural vector for many members of rickettsiae such as *Anaplasma marginale, E. canis* or *R. rickettsii*. It is a natural vector for *Borrellia burgdorfi, Babesia microtia* and other Ehrlichia species.

*Ixodes scapularis* tick cell culture lines can be established and maintained in vitro. The cells are loosely adherent and can be continually passaged. Several cell lines that are different from one another can be obtained from a single egg mass from one female. Cell lines that are different from one another can also be obtained from using embryos of different ages. *Ixodes scapularis* cell lines can be characterized using morphology, karyotype and isozyme profile using standard methods as described in Example 1.

Several cell lines isolated from *Ixodes scapularis* ticks were obtained from white-tailed deer in Minnesota near the St. Croix River and in Polk County, Wis. These cell lines are designated IDE. The cell lines established from ticks from Minnesota and Wisconsin vary in morphology and isozyme profile. The cell lines are undifferentiated cells and each cell line can contain more than one cell type.

An example of a tick cell line isolated from ticks from Minnesota and Wisconsin is designated IDE8. IDE8 cells are characterized morphologically by the presence of distinctive fine wavy membrane stacks within vacuoles in the cytoplasm and have long branching pseudopodia. An electron micrograph of cell line IDE8 is shown in FIG. 1A. The cell line is diploid and the modal number of chromosomes is 2n=28 with two sex chromosomes. The IDE8 cells after passage 17 have the following isozyme profile: lactate dehydrogenase isozyme (LDH) with pI of 6.8, 7.0 and 7.5; malate dehydrogenase isozyme (MDH) with pI of 8.5, 8.1, 5.1, 6.1, and 6.7; and malic enzyme (ME) isozyme with pI of 5.1, 5.3, 5.6, 6.2, 6.4 and 6.5. The cells grow firmly attached to the substrate with a population doubling time of approximately 6 days. The cell line has been deposited with the American Type Culture Collection in Rockville, Md. and given an Accession No. CRL 11973, on Aug. 24, 1995.

Cell lines have also been established from *Ixodes scapularis* ticks obtained from Dr. James Oliver Jr. (Georgia Southern University, Statesboro, Ga.). Cell lines from these ticks are designated ISE. Cell lines from the ticks from Georgia also vary in morphology and isozyme profile.

An example of a cell line isolated from the ticks from Georgia is designated ISE6. ISE6 cells are much less adherent than IDE8 cells and are spindle shaped. They are often seen in close association with one another as shown in FIG. 1B. The cell line is diploid with modal chromosome number 2n=28 with two sex chromosomes. In a western blot analysis, the antigenic profile of ISE6 is similar to that for other *I. scapularis* cell lines using antisera from hamsters or rabbits immunized with *I. scapularis* cells. The cell line grows with a population doubling time of about 8 to 10 days. The cell line has been deposited with the American Type Culture Collection in Rockville, Md. and given Accession No. CRL 11974, on Aug. 24, 1995.

*Ixodes scapularis* cell lines are preferably maintained and passaged in a medium that supports the growth of invertebrate cells. The preferred medium is an L15B medium with a pH of 7.0. (Munderloh and Kurtti, Exp. Appl. Acarology 7:219 (1989)) L15B medium is a modification of Leibovitz's L15 medium (Leibovitz 1963 Am. J. Hyg. 78:173–180) containing additional glucose, amino acids, vitamins and trace minerals. The complete L15B medium also includes about 80 mM glucose, about 10% tryptose phosphate broth (Difco Laboratories, Detroit, Mich.), about 3–5% fetal bovine serum (Gibco, Grand Island, N.Y.), and about 0.1% bovine lipoprotein concentrate (ICN, Irvine, Calif.). Cell lines are cultured at about 31° to 35° C. temperature.

Cells can be subcultured at ratios of about 1:3 to about 1:20. The first subculture can be initiated about 6–12 months after primary culture. After establishment of cell lines, they are passaged at about every 2 to 3 weeks.

*Ixodes scapularis* cell cultures can also be cultivated using standard large scale culture techniques. These large scale culture techniques include the use of cell factories, bioreactors, hollow fiber tubes and beads. Other culture methods include growing the tick cells in wells or slides or on other readily accessible surfaces.

*Anaplasma marginale*

*Anaplasma marginale* is a tick-transmitted disease agent of the order Rickettsiales and the causative agent of the disease of *anaplasmosis*. *A. marginale* invades and multiplies in erythrocytes of cattle causing mild to severe anemia.

A. marginale can be transmitted by several species of Dermacentor ticks. The bovine and tick stages of A. marginale are known and described morphologically. Bovine erythrocytes have A. marginale-containing inclusion bodies at a peripheral location. The inclusion bodies contain 1 to 8 organisms. In the tick, the organisms have two stages including an electron dense stage and a reticulated stage. The organisms grow in membrane bound inclusions called colonies. The colonies often contain hundreds of organisms and are found in gut and salivary gland cells of naturally-infected ticks.

Anaplasma marginale isolates obtained from infected cattle can be used to infect Ixodes scapularis tick cell culture. This result was surprising because Ixodes scapularis is not a natural vector for A. marginale. While not meant to limit the invention, it is believed that *Ixodes scapularis* is a more primitive tick and therefore may support the growth of many members of rickettsiae even though *Ixodes scapularis* is not the natural vector for some of these microorganisms.

In a method of the invention, *A. marginale* is incubated with *Ixodes scapularis* tick cell culture. The preferred *Ixodes scapularis* cell lines are the IDE8 cell line and the ISE6 cell line. *A. marginale* inoculum can be obtained from infected cattle with about 10 to 100% parasitemia, preferably about 30 to 50% parasitemia. About 1.5 ml of bovine red blood cells are lysed by freeze thawing. 8*A. marginale* inoculum can also be obtained from *A. marginale* passaged in tick cell culture. *A. marginale* passaged in tick cell culture is available from Dr. Uli Munderloh University of Minnesota, St. Paul, Minn. and Dr. Katherine Kocan and Dr. Edmour Blouin, Oklahoma State University, Stillwater, Okla. Infected tick cell cultures with up to 100% infected cells can be incubated with uninfected tick cells at a ratio of about 1:3 to about 1:20.

*A. marginale* Virginia isolate (VAM) from infected cattle can be obtained from Dr. Katherine Kocan, Oklahoma State University, Stillwater, Okla. Other isolates of *A. marginale* from diverse geographic areas are known and described by McGuire et al., Inf. Imm. 45:697 (1984). *A. marginale* isolates from Florida and Oklahoma are also available from Dr. Katherine Kocan, Oklahoma State University, Stillwater, Okla.

The *A. marginale* inoculum is incubated with *Ixodes scapularis* cell lines in a culture medium including an organic buffer. Preferably, the culture medium is a medium that provides for the growth of invertebrate cells such as *Ixodes scapularis* tick cells. The preferred medium is the L15 medium as described by Munderloh and Kurtti, Exp. Appl. Acarol 7:219 (1989). The preferred medium is also supplemented with about 80 mM glucose, about 3–5% fetal bovine serum, about 10% tryptose phosphate broth and about 0.1% bovine lipoprotein. Preferably about 10 to 15 millimolar organic buffer is also included for growth of *A. marginale*. About 25 mM organic buffer is toxic to the invertebrate cells. Organic buffers include 3-(N-morpholino)-propanesulfonic acid (MOPS), and HEPES.

The *A. marginale*-infected *Ixodes scapularis* cell cultures are preferably incubated under conditions providing for enhanced $CO_2$ levels. One method of culturing *A. marginale*-infected tick cell cultures includes incubating the cells at reduced oxygen of about 17% and increased $CO_2$ of about 3 to 5% in a candle jar. Alternatively, the *A. marginale* cell cultures can be incubated with a culture medium including a source of $HCO_3^-$. Preferably about 0.1 to 0.25% of $HCO_3^-$ is included in the culture medium.

The cells are incubated at about 31° to 34° C. for about 2 to 4 weeks until growth of *A. marginale* is first detected. Growth of *A. marginale* from infected bovine blood is first seen about 1 month post infection. Growth of *A. marginale* that has been passaged in culture can be detected in about one week.

Growth of *A. marginale* can be detected by several methods. Growth of *A. marginale* can be detected by light microscopic examination of a stained cell sample. Cell samples can be stained with Giemsa, Wright's, Diff-Quik, and fluorescently-labelled antibodies. Growth of *A. marginale* is detected in tick cell cultures when about 2 to 100% of the tick cells are infected. Alternatively, growth of *A. marginale* can be detected by the presence of a cytopathic effect on the tick cell culture.

*A. marginale* in infected tick cell culture is seen in both the dense and reticulated forms within typical colonies. After a two to four passages, the infection rate in the tick cell culture increased from 10% to approximately 100% of the tick cells. The *A. marginale* observed in the cultured tick cells is morphologically similar to that described in naturally-infected ticks. Tick cells with large inclusion bodies can be observed by light and electron microscopy. Tick cells with large colonies degenerate and lyse to release the inclusion bodies.

The growth of *A. marginale* can also be detected and/or quantitated using a detectably labeled probe as described by Ge et al., J. Vet. Diag. Investigations Vol. 7 (October 1995). Methods used to detect and quantitate *A. marginale* tick cells using probes include slot blot and in situ hybridization. Hybridization detection methods are known to those of skill in the art and are described in Sambrook et al., *A Guide to Molecular Cloning: A Laboratory Manual*, Cold Spring Harbor Laboratory (1989). An example of slot blot hybridization is described in Example 2.

Hybridization conditions for slot blot hybridization are: treated DNA samples bound to nylon membranes were treated with a prehybridization solution containing sarkosyl and salmon sperm DNA. After blocking, the membranes are soaked in a hybridization solution including 30 ng/ 100 sq. cm of membrane of digoxigenin labelled probe. After an overnight exposure, the membranes are washed 4 times in SSC at 68° C. Hybrid formation is detected with alkaline phosphatase conjugated anti-digoxigenin antibody and substrates 5-bromo-chloro-3-indolyl phosphate and nitroblue tetrazolium salt.

The amount of *A. marginale* in infected blood cells and tick cell culture can be quantitated by determining the amount of detectably labeled probe that hybridizes to a sample containing 0.01 ng or 1,000 to 10,000 copies of Anaplasma genomic DNA. The amount of probe hybridized can be quantitated using standard methods depending on the detectable label on the probe. For example, hybridization of a radioactively labeled probe can be quantitated using scanning densitometry. Digoxigenin labeled probes can be detected and quantitated using densitometry.

A probe and/or primer specific for *A. marginale* can be designed from known DNA sequence information for *A. marginale*-specific proteins using standard methods as described in Sambrook et al. cited supra. DNA sequences encoding *A. marginale*-specific proteins include a DNA sequence for the *A. marginale* msp-1β gene as described by Barbet et al., *Infection and Immunity,* 59:971 (1991). Primers and probes can be designed using standard methods including the use of commercially available software.

A probe of the invention hybridizes to and is complementary to all or a portion of a nucleic acid sequence encoding the *A. marginale* msp-1β gene. The probe can be complementary to or hybridize to a portion of the nucleic acid sequence that encode the msp-1β gene as long as the probe specifically detects the presence of the msp-1β gene and/or A. marginale. The probe can be about 15 nucleotides long up to a full length probe for the msp-1β gene. The probes are preferably 100% complementary to the nucleic acid encoding msp-1β gene, however some mismatches can be present depending on the length of the probe. About 1 to 3 mismatches in a probe of about 20 to 30 nucleotides long can be present as long as hybridization conditions are adjusted to account for mismatches. Hybridization conditions can be adjusted to take into account mismatches in accord with known principle as described in Sambrook et al., *A Guide To Molecular Cloning*, Cold Spring Harbor, N.Y. (1989).

Probes can be prepared by automated synthesis, PCR and/or by restriction enzyme digestion. Probes can be labeled with a detectable label such as radiolabeled nucleotides, digoxigenin labeled nucleotides and fluorescently labeled nucleotides. Methods of labeling probes are known to those of skill in the art and are described by Sambrook et al. cited supra.

A preferred probe is a 409 base pair fragment of the A. marginale msp-1β gene as described by Barbet et al. cited supra. The probe is labeled with digoxigenin labeled nucleotides (11-dUTP) and prepared using PCR. The probe was prepared using primers as described by Stich et al., *Journal of Medical Entomology*, 30:781 (1993). The primers have the following sequence:
BAP-2 5'-GTA TGG CAC GTA GTC TTG GGA TCA-3' (SEQUENCE ID NO:1)
AL34S 5'-CAG CAG CAG CAA GAC CTT CA-3' (SEQUENCE ID NO:2)
A probe can be prepared as described in Example 2.

Probes are useful to detect and/or quantitate A. marginale using hybridization methods. Hybridization methods include slot blot, dot blot, northern blot and in situ hybridization. The preferred method is slot blot hybridization.

Growth of A. marginale can also be detected with polymerase chain reaction (PCR). PCR can be conducted on isolated nucleic acids such as DNA or RNA or by in situ methods. Primers can also be designed based upon the DNA sequence of the A. marginale msp-1β gene. Primers can be designed using a known sequence or using commercially available computer programs. Primers typically are complementary to and/or hybridize to a 5' region and/or a 3' region of the nucleic acid sequence. The primers can be used to amplify all or a portion of the DNA or cDNA encoding msp-1β. Primers can be used to make probes, to detect expression levels of msp-1β and to detect the presence of A. marginale-specific DNA. Primers preferably have at least 15 nucleotides that are 100% complementary to the nucleotide sequence. The primers can also have additional sequences preferably at ends of the primer that include restriction enzyme sites and the like that are not complementary to the nucleic acid sequence to be amplified. Primers are preferably about 15 to 50 nucleotides long and can be prepared by automated synthesis.

The preferred primers amplify a 409 base pair fragment of A. marginale msp-1β gene and have the following sequence:
BAP-2 5'-GTA TGG CAC GTA GTC TTG GGA TCA-3'
AL34S 5'-CAG CAG CAG CAA GAC CTT CA-3'
PCR can be conducted as described in Example 2. Growth of A. marginale is detected in tick cell cultures by detecting a 409 base pair PCR product specific for A. marginale.

PCR can be utilized to diagnose and/or to detect infection with A. marginale. Total DNA from a blood sample from an animal suspected of having an A. marginale infection can be extracted and analyzed for A. marginale DNA as described above. Blood samples from animals acutely infected as well as carrier animals can be analyzed for the presence of A. marginale-specific DNA.

The invention also includes tick cell cultures infected with A. marginale. These infected tick cell cultures are useful as diagnostic tools for assays including ELISA, indirect fluorescent antibody tests, latex agglutination and complement fixation tests. It is preferred that about $10^2$ to $10^6$ number of cells are present on a slide with about 10 to 100% cells infected, preferably about 80 to 100% cells infected.

For example, infected tick cell cultures can be utilized as slides in an indirect fluorescent antibody test. Infected tick cell cultures grown on slides can be fixed and then incubated with antiserum from cattle suspected of being infected with A. marginale. Titers of anti-A. marginale antibodies can also be established using an ELISA assay with infected tick cells or antigen preparation from infected tick cells. Diagnostic assays also include methods such as in situ PCR.

Infected tick cell cultures can be grown on slides, in wells and on other readily accessible surfaces. Infected tick cell cultures can also be grown using large scale cultivation techniques as described previously. It is believed that a great enhancement in yield of A. marginale can be obtained at a much lower cost because of an increase in the number of microorganisms present per infected tick cell as well as the number of infected tick cells in a culture compared with bovine erythrocytes. Many infected tick cells contain large inclusion bodies with numerous A. marginale compared with about 4 to 8 A. marginale per infected red blood cell.

In addition, the ability to grow infected tick cells on a large scale can provide for a further enhancement in yield at a much lower cost. An infected cow yields about 3 liters of infected bovine blood containing about 30 to 50% parasitemia. An infected cow costs about $2400 to initiate infection and to maintain in the infected state. In contrast, large scale in vitro production would allow 100% infection of more than $10^{10}$ cells or more with enhanced yield per cell, therefore greatly reducing in the cost to produce A. marginale for vaccines or antigen preparations.

The invention also includes vaccine and antigen preparations of A. marginale grown in *Ixodes scapularis* tick cell culture. Vaccine preparations can include whole microorganisms or subunit vaccines including antigen preparations derived from A. marginale. The vaccine preparations can be heat killed or live attenuated microorganisms. The vaccine formulations can be prepared in accord with methods standard in the art.

Preferably, vaccines and antigen preparations are made from A. marginale passaged in *Ixodes scapularis* tick cells from about 2 to 20 times and that still retain infectivity for cattle and/or can be transmitted by the natural vector. A. marginale passaged in tick cells for 2 to 4 passages retains infectivity for cattle and can be transmitted from infected cattle to uninfected animals by Dermacentor ticks. The infectivity of passaged A. marginale can be determined using standard methods as described in Example 3.

Preferably, the vaccine formulations and antigen preparations are essentially free of bovine erythrocyte antigens and other bovine pathogens. Vaccine and antigen preparations prepared from infected bovine erythrocytes can be contaminated with bovine erythrocyte membranes and antigens that can result in formation of an immune response to bovine blood cells. This immune response to bovine red blood cells can cause isohemolytic disease especially in newborn calves. Contamination of bovine blood with bovine pathogens may also be likely because of the use of large amounts of bovine blood.

In contrast, *A. marginale* grown in tick cell culture can be produced on a large scale with little or no contamination with bovine erythrocyte antigens or other bovine pathogens. Electron micrographs of infected tick cultures indicate that contamination with bovine erythrocytes or other bovine pathogens has not been detected. Because only a small amount of bovine blood is used as inoculum and *A. marginale* can be passaged several times, costly separation from bovine red blood cells components and contaminants can be avoided.

The vaccine and antigen preparations can also include *Ixodes scapularis* tick cell antigens. The presence of *Ixodes scapularis* tick cell antigens may provide an additional protective immune response. The presence of *Ixodes scapularis* tick cell antigens includes antigens with molecular weights of about 40 kDa, 43 kDa, 50 kDa and greater than 120 kDa as determined by SDS PAGE. Optionally, the vaccine and/or antigen preparations can be further purified from tick cell antigens using antibodies specific for *A. marginale* and methods known to those of skill in the art.

Vaccine and antigen preparations can also be prepared at higher yield per infected cell than in bovine erythrocytes. As described previously, it is believed that higher yields can be obtained in tick cell cultures because the cells can be grown on a large scale, up to 100% of the cells can be infected and more microorganisms are produced per infected cell.

The vaccine and/or antigen preparation is combined into a formulation in an amount effective to provide for a protective immune response against infection with *A. marginale*. A protective immune response against *A. marginale* decreases the clinical symptoms of anaplasmosis. Clinical symptoms of anaplasmosis include a reduction in packed red cell volume of about 25 to 80% and parasitemia of the red blood cells of about 15 to 70%. A decrease in the symptoms of anaplasmosis includes prevention of the reduction in the packed red cell volume and a decrease in % parasitemia. Preferably, a protective response includes packed red cell volume change of 25% or less compared with control animals and/or a decrease in parasitemia to about 15 to 25% of the red blood cells or less. Measurements of packed red cell volume and % parasitemia are conducted using standard methods. Preferably, about 1 to 1000 mg/kg of body weight of the vaccine is administered, more preferably about 1 to 50 mg per animal.

Vaccine and antigen preparations can be prepared from a single *A. marginale* isolate or from several *A. marginale* isolates from different geographic areas. It is preferred that the vaccine formulation provides for crossprotection against several isolates of *A. marginale* from geographically diverse regions. However, it is not necessary to achieve a crossprotective effect. Separate vaccine and antigen preparations can be prepared from isolates of *A. marginale* from each geographic location.

Vaccine preparations of *A. marginale* and antigen preparations are combined with physiologically acceptable carriers to form vaccines. The physiologically acceptable carriers include buffered salt solutions, phosphate buffered saline, and cell culture media. Optionally, the vaccine formulation can include adjuvants such as alum, IPSCOMS, Complete Freund's adjuvant, Incomplete Freund's adjuvant and saponin.

The vaccines are administered by a variety of routes including intravenously, intraperitoneally, intramuscularly, and subcutaneously. The preferred route of administration is subcutaneous. The vaccine can be administered in a single dose or multiple dose until a protective effect is achieved.

Antigen preparations are also useful to prepare diagnostic tools such as ELISA plates, antibody card tests, complement fixation tests and the like. Antigen preparations can be prepared from *A. marginale* grown in *Ixodes scapularis* tick cell culture as described in Example 5 and by standard methods. It is preferred that antigen preparations include *A. marginale* antigen having molecular weights of about 80 kDa, 30 kDa and 28 kDa as determined by SDS PAGE.

In a preferred version, *A. marginale* Virginia isolate from infected bovine blood stored at Oklahoma State University is cultured with cell line IDE8 at about 34° C. *A. marginale* is cultured with the tick cells in L-15B medium supplemented with about 3 to 5% fetal bovine serum, 10% tryptose phosphate broth, 0.25% $NaHCO_3$ and 10 mM MOPS. The cells are incubated for about 30 days and then one part infected cells are passaged with 10 parts uninfected tick cells. After about 2 to 4 passages (i.e., about 6 to 12 weeks), the *A. marginale* is harvested as described in Example 5 and used as a heat killed vaccine or antigen preparation.

Ehrlichiae

Ehrlichiae include species that are tick-transmitted disease agents. Ehrlichiae include species that infect and multiply in white blood cells. The monocytic Ehrlichiae include *E. canis, E. chaffeensis, E. risticii, E. sennetsu*, which primarily infect blood monocytes. *E. canis* is a tick-transmitted disease agent that causes ehrlichiosis, sometimes called canine tropical pancytopenia. *E. chaffeensis* infects humans and causes human ehrlichiosis. *E. risticii* infects horses and cause Potomac Horse Fever. *E. sennetsu* infects humans and is the causative agent of *Sennetsu ehrlichiosis*. All of these species are closely related antigenically.

In a method of the invention, monocytic Ehrlichiae species such as *E. canis* are incubated with *Ixodes scapularis* tick cell culture. The preferred tick cell culture line is the IDE8. *E. canis* inoculum can be obtained from infected dogs by collecting whole peripheral blood, and is available from Dr. Sidney Ewing, Oklahoma State University, Stillwater, Okla. *E. canis* is also available from ProtaTek International, Inc., St.Paul, Minn. *E. canis* inoculum can also be obtained from *E. canis* passaged in *Ixodes scapularis* cell culture from Dr. Munderloh, University of Minnesota, St. Paul, Minn. Infected tick cell cultures with up to 100% infected cells can be incubated with uninfected tick cells at about a ratio of 1:3 to about 1:20.

A monocytic Ehrlichia species is incubated with *Ixodes scapularis* tick cells in a culture medium including an organic buffer. Preferably, the culture medium is a medium that provides for the growth of invertebrate cells such as *Ixodes scapularis* tick cells. The preferred medium is L15B medium as described previously. Preferably, about 10 to 15 millimolar organic buffer is also included to provide for growth of *E. canis*. Organic buffers include MOPS, and HEPES. The culture medium is also supplemented with a source of $HCO_3^-$, preferably about 0.1% to about 0.25% $NaHCO_3$.

The monocytic Ehrlichia-infected *Ixodes scapularis* cell cultures are preferably incubated under conditions of reduced oxygen and enhanced $CO_2$. One method of growing a monocytic Ehrlichia species in tick cell culture includes incubating the infected tick cells at reduced oxygen of about 17% and increased $CO_2$ of about 3 to 5%. The cells are incubated at about 34° to 35° C. for about 3 to 5 weeks until growth of the monocytic Ehrlichia is detected.

Growth of monocytic Ehrlichiae in *Ixodes scapularis* tick cell culture can be detected by a variety of methods. Growth of the *E. canis* can be seen at about one to five weeks after inoculation. Growth of monocytic Ehrlichiae can be detected by light microscopic examination of a stained cell sample. Cell samples can be stained with Giemsa, Wright's, Diff-Quik and Leishman's stain. Alternatively, growth can be detected by electron microscopy, polymerase chain reaction, indirect fluorescent antibody tests or other serodiagnoses, or by flow cytometry.

The growth or presence of monocytic Ehrlichiae can be detected using polymerase chain reaction as described in Chen et al., J. Clin. Microbiol. 32:584 (1994). Primers and probes can be designed that are specific for Ehrlichiae species 16s rDNA. Primers specific for *E. canis* includes primers: ECAN5forward 5' CAA TTA TTT ATA GCC TCT GGC TAT AGG A 3' and ESPEC3reverse 5' TAT AGG TAC CGT CAT TAT CTT CCC TAT 3' (designed by Dr. George Murphy). Primers specific for other Ehrlichiae species are described in Chen et al. cited supra. DNA is amplified during 30 cycles of denaturing for 45 sec. at 94° C., annealing for 30 sec. at 55° C., and extension for 90 sec. at 72° C. A single final extension cycle at 72° C. for 10 min. concludes the program. For both templates, the expected size of the amplicon is ~400 bp.

Growth of the monocytic Ehrlichiae can be quantitated using the following method. Cultures are sampled weekly by removing a small volume of suspended cells. The cell suspensions are centrifuged (60 g) onto glass microscope slides using a Cytospin (Shandon Southern Instruments, Seewickly, Pa.). After drying and methanol fixation, the cell spreads are stained with Giemsa stain. Growth is quantitated by determining the proportion of cells that are infected and approximating the number and size of ehrlichial colonies per cell.

The invention also includes tick cell cultures infected with monocytic Ehrlichiae. The infected tick cell cultures are useful in diagnostic assays. The infected tick cell cultures can be grown on slides, in wells, and on other readily accessible surfaces. It is preferred that cell line IDE8 are grown on slides and infected with *E. canis*. It is preferred about $10^2$ to $10^6$ cells are present on a slide with about 2 to 100% of cells infected, preferably about 60 to 80%. Infected tick cell cultures can be especially useful in serodiagnosis methods, especially the indirect fluorescent antibody assay.

Infected tick cell culture can also be grown using large scale cultivation techniques as described previously.

Antigen preparations can include whole microorganisms, and/or portions thereof. Antigen preparations can be prepared in accord with methods standard in the art. Antigen preparations can be prepared as described in Example 9.

Preferably, antigen preparations of monocytic Ehrlichiae are made from monocytic Ehrlichiae passaged in *Ixodes scapularis* tick cell culture from about 5 to 15 times and that retain infectivity for animals and/or cell lines such as DH82 cell line. *E. canis* passaged in tick cells about 1 to 10 passages retains infectivity for dogs. The infectivity of passaged *E. canis* and other monocytic Ehrlichiae can be determined in animals such as dogs or in cell lines such as DH82 cells by standard methods as described in Example 8. DH82 cells are available from the Viral and Rickettsial Disease Division, Centers for Disease Control and Prevention, Atlanta, Ga.

Preferably, antigen preparations for *E. canis* are essentially free of canine antigens and/or other canine pathogens. Antigen preparations prepared from infected dogs or DH82 cells can be contaminated with canine antigens that can result in a formation of an immune response to the dog antigens. This immune response to dog antigens can cause adverse immunological responses in vaccinated dogs. Contamination of dog blood or dog cell lines with dog pathogens may also be likely because of the large amounts of blood or canine cell lines necessary to prepare antigen preparations.

In contrast, *E. canis* grown in tick cell culture can be produced on a large scale with little or no contamination with canine antigens or other canine pathogens. Electron micrographs of infected cultures indicate that contamination with dog pathogens has not been detected. Because only a small amount of dog blood is used as inoculum and *E. canis* or other monocytic Ehrlichiae can be passaged several times, costly separation of the *E. canis* antigens from canine cells and contaminants can be avoided.

The antigen preparations can also include *Ixodes scapularis* tick cell antigens. The presence of *Ixodes scapularis* tick cell antigens may provide an additional protective immune response. Optionally, the vaccine and/or antigen preparations can be further purified from tick cell antigens using antibodies specific for *E. canis* and methods known to those of skill in the art.

Antigen preparations are useful to prepare diagnostic tools such as ELISA plates, antibody card tests, complement fixation tests and the like. Antigen preparations can be prepared from the monocytic Ehrlichiae grown in *Ixodes scapularis* tick cell culture as described in Example 9 and by standard methods.

In a preferred version, *E. canis* from infected dog blood is cultured in cell line IDE8 at about 33° to 35° C. *E. canis* is cultured with the tick cells in L15B medium supplemented with 10 mM MOPS and 0.25% $NaHCO_3$. The cells are incubated in a candle jar at about 17 percentage oxygen and about 3 percentage $CO_2$. The cells are incubated for about 2 to 4 weeks and then one part infected cells are passaged with ten parts uninfected tick cells. After about 2 to 3 passages (i.e., about 4 to 8 weeks) the *E. canis* is harvested as described in Example 9 and used as a heat killed vaccine or antigen preparation.

Rickettsiae

Rickettsiae includes species that are tick-transmitted disease agents. A tick-transmitted disease agent is *R. rickettsii* which causes Rocky Mountain Spotted Fever in humans. *R. rickettsii* is transmitted by *Dermacentor variabilis*, also known as the American dog tick or common wood tick. *Ixodes scapularis* is not a natural vector for *R. rickettsii*. *R. rickettsii* obtained from infected tick vectors or infected vertebrate hosts can be grown in *Ixodes scapularis* tick cell culture.

In a method of the invention, Rickettsiae such as *R. rickettsii* are incubated with *Ixodes scapularis* tick cell culture. The preferred culture is the IDE8 tick cell line or the ISE6 cell line. *R. rickettsii* inoculum can be obtained from infected vector tick or mammalian host by collecting blood from infected mammalian host or tissues from tick. *R. rickettsii* is also available from American Type Culture Collection. *R. rickettsii* inoculum can also be obtained from *R. rickettsii* passaged in *Ixodes scapularis* cell culture, embryonated hen's eggs and/or mammalian cell culture. Tick cell cultures with about 80 to 100%. infected cells can be incubated with uninfected tick cells with a ratio of about 1:3 to 1:20.

The Rickettsiae are incubated with *Ixodes scapularis* tick cells in a culture medium including an organic buffer. Preferably, the culture medium is a medium that provides for the growth of invertebrate cells such as *Ixodes scapularis* tick cells. The preferred medium is L15B medium as described previously. Preferably, about 10 to 15 millimolar organic buffer is also included to provide for growth of Rickettsiae such as *R. rickettsii*. Organic buffers include MOPS and HEPES.

The Rickettsiae-infected *Ixodes scapularis* cell cultures can be incubated under normal atmospheric conditions.

Optionally, the cultures may be incubated under conditions of reduced oxygen and enhanced $CO_2$. One method of growing Rickettsiae in Ixodes scapularis tick cell culture includes incubating the cells in reduced oxygen at about 17 percentage and increased $CO_2$ of about 3 to 5%. Optionally, the infected tick cell cultures can also be incubated with enhanced levels of $CO_2$. Preferably, the medium contains about 0.1% to 0.25% $HCO_3^-$. The infected cells are incubated at about 31° to 35° C. for about 1 to 4 weeks until growth of Rickettsiae is detected.

Growth of Rickettsiae such as R. rickettsii in Ixodes scapularis can be detected by a variety of methods. Growth of R. rickettsii can be seen at about 1 to 4 weeks. Growth of Rickettsiae can be detected by light microscopic examination of a stained cell sample. Cell samples can be stained with Giemsa, Wright's, Diff-Quik and Giminez. Alternatively, growth can be detected by electron microscopy, immunofluorescent staining and flow cytometry.

Growth of Rickettsiae can be quantitated using the following method. Cultures are sampled weekly by removing a small volume of suspended cells. The cell suspensions are centrifuged (60 g) onto glass microscope slides using a Cytospin (Shandon Southern Instruments, Seewickly, Pa.). After drying and methanol fixation, the cell spreads are stained with Giemsa stain. Growth is quantitated by determining the proportion of cells that are infected and approximating the number and size of rickettsia per cell.

The invention also includes Rickettsiae-infected tick cell cultures. The infected tick cell cultures are useful in diagnostic assays. The infected tick cell cultures can be grown on slides, in wells or on other readily accessible surfaces. It is preferred that the cell line IDE8 are grown on slides and infected with R. rickettsii. It is preferred about $10^2$ to $10^6$ number of cells are present with about 2 to 100%, preferably 60 to 80% of cells infected.

Infected tick cell cultures can also be grown using large scale cultivation techniques as described previously.

Vaccine preparations can include whole microorganisms, antigen preparations and/or subunit vaccines. The vaccines can be heat killed or live attenuated microorganisms. Vaccine formulations can be prepared in accord with methods standard in the art. Preferably, heat killed vaccines and antigen preparations of the Rickettsiae are made from R. rickettsii passaged in Ixodes scapularis tick cells from about 1 to 3 weeks and that retain infectivity for mammalian cell culture and/or embryonated eggs. The infectivity of passaged R. rickettsii in tick cells can be determined in mammalian cell culture or embryonated eggs using standard methods.

Preferably, the vaccine and antigen preparations are essentially free of mammalian antigens and other mammalian pathogens. The vaccine and antigen preparations prepared from embryonated eggs and/or mammalian cell culture can be contaminated with mammalian antigens that can result in formation of an immune response to these antigens. The immune response to these antigens can cause an adverse immunological response in vaccinated humans. Contamination of mammalian cell culture or embryonated eggs with other human pathogens may also be likely.

In contrast, Rickettsiae grown in tick cell culture can be produced on a large scale with little or no contamination with human or egg antigens. Electron micrographs of infected tick cell cultures indicate that contamination with other pathogens has not been detected. R. rickettsii and other species of Rickettsiae can be passaged several times and grown on a large scale, eliminating costly separation from mammalian and/or egg components and contaminants.

The vaccine and antigen preparations can also include Ixodes scapularis tick cell antigens. The presence of Ixodes scapularis tick cell antigens may provide an additional protective immune response. Optionally, the vaccine and/or antigen preparations can be further purified from tick cell antigens using antibodies specific for R. rickettsii and methods known to those of skill in the art.

The vaccine and/or antigen preparation is combined into a formulation in an amount effective to provide for a protective immune response against infection with R. rickettsii. A protective immune response against R. rickettsii protects against infected tick challenge and involves a humoral and cell mediated immune response. A protective immune response can be detected or measured by microagglutination or indirect fluorescent antibody titers. About 6 million R. rickettsii or 22 micrograms of rickettsial protein per dose are administered as a vaccine to a human. (Ascher et al. 1978 J. Infect. Dis. 138:217–221.)

Vaccine formulations can be prepared using formalin killed R. rickettsii and/or antigen preparations. Formalin killed Rickettsiae and/or antigen preparations are combined with physiologically acceptable carriers to form vaccines. The physiologically acceptable carriers include phosphate buffered saline, and 0.85% saline. Optionally, the vaccine formulations can include adjuvants such as alum, Saponin QS21, monophosphoryl lipid A and trehalose dimycolate.

The vaccines are administered by a variety of routes including subcutaneously, intravenously, and intramuscularly. The preferred route of administration is subcutaneous in the deltoid region. The vaccine can be administered in a single dose or multiple doses until a protective effect is achieved. It is preferred that the vaccine stimulate a protective immune response to infection with R. rickettsii. It is also preferred that the vaccine ameliorate and prevent the development of the symptoms of Rocky Mountain Spotted Fever.

Antigen preparations are also useful to prepare diagnostic tools such as ELISA plates, antibody card tests, complement fixation tests and the like. Antigen preparations can be prepared from R. rickettsii grown in Ixodes scapularis tick cell culture by standard methods. The antigen preparations and the diagnostic tools so formed such as ELISA plates or infected tick cell culture slides can be utilized in methods to diagnose the presence of infection with Rickettsiae such as R. rickettsii.

In a preferred version, R. rickettsii from infected ticks is cultured with cell line IDE8 at about 34° C. R. rickettsii is cultured with the tick cells in L15B medium supplemented with 3 to 5% fetal bovine serum, 10% tryptose phosphate broth, 0.1% bovine lipoprotein concentrate and 10 mM MOPS. The cells are incubated for about 7 to 14 days and then one part of infected cells are passaged with 50 parts uninfected tick cells. After about 5 to 15 passages, the R. rickettsii is harvested using standard methods and used as heat killed vaccine or antigen preparation.

All publications and patent applications in this specification are indicative of the level of ordinary skill in the art to which this invention pertains. All publications and patent applications are herein incorporated by reference to the same extent as if each individual publication or patent application was specifically and individually indicated by reference.

It will be apparent to one of ordinary skill in the art that many changes and modifications can be made in the invention without departing from the spirit or scope of the appended claims.

EXAMPLE 1

Establishment, Maintenance and Description of Cell Lines from Ixodes Scapularis

Cell lines were established from embryonic tick cell cultures. Cell lines were maintained and characterized.

Ticks

Engorged female black-legged ticks (*I. scapularis*) were collected from hunter-killed white-tailed deer (*Odocoileus virginianus*) in Minnesota near the St. Croix River and in Polk County, Wis. They were surface-disinfected as described (Kurtti et al., J. Invert. Path. 42:334, 1983) and individually placed into wells of a sterile 12-well cell culture plat. Plates were held in a desiccator over sterile distilled water under a 16-hr light/8-hr dark program at 25° C. during light and 20° C. during dark periods. The onset of oviposition was recorded for each tick and used to determine the age of the embryos, i.e., age in days postonset of oviposition (-days po). Embryos from these ticks were used to establish cell lines coded IDE.

Gravid southern black-legged tick females (*I. scapularis*) were obtained from Dr. J. H. Oliver, Jr. (Georgia Southern University, Statesboro, Ga.). They were surface-disinfected and held for oviposition as described above. Embryos from these ticks were the source material for cell lines coded ISE.

Primary Cultures

Nunc plastic ware (Nunc, Roskilde, Denmark) was used throughout this study. The 25-cm$^2$, 50-ml volume flasks provided a ratio of air space to medium volume that was favorable to tick cell growth, and the screw caps did not crack during the many months until primary cultures were subcultured for the first time. Twenty-three to 27 days po, egg masses were separately scooped into sterile 35-mm-diameter plastic Petri dishes and weighed. The eggs were gently crushed in 0.5 ml of L-15B medium (Munderloh and Kurtti, cited supra, 1989), pH ~7, containing 80 mM glucose and supplemented with 10% tryptose phosphate broth (TPB; Difco Laboratories, Detroit, Mich.), 20% heat-inactivated fetal bovine serum (FBS; GIBCO, Grand Island, N.Y.), 100 units/ml penicillin and 100 $\mu$g/ml streptomycin (GIBCO). This medium was referred to as primary culture medium. Tissues and egg shells were resuspended in 10 ml of the same medium and centrifuged once at 100 g. Pellets from egg masses weighing 40 mg or more were divided into 2 fractions that were separately seeded into 25-cm$^2$ flasks in 5 ml of primary culture medium. The top layer contained most of the egg shells but also a substantial amount of embryonic tissues. The bottom layer contained the majority of the tissue fragments and only a few shells. Pellets from smaller egg masses were not subdivided but transferred to a single 25-cm$^2$ flask. Neither culture flasks nor media were "conditioned" (Yunker, Arboviruses in Arthropod Cells, In Vitro Vol. 1, CRC Press pp. 35–37, 1987) prior to use. Primary cultures were coded IDE or ISE, as appropriate, followed by a number and incubated at 31 C.

Establishment of Cell Lines

All cultures were fed 1 week after initiation by replacing 4 ml of the primary culture medium with 5 ml of fresh primary culture medium. Thereafter, cultures were fed once a week with 5 ml fresh primary cultures medium. The first subculture was carried out 6–12 months after initiation of the primary culture. The antibiotics were omitted, the concentration of serum in the medium was reduced to 5%, and 0.1% of bovine lipoprotein concentrate (ICN, Irvine, Calif.) was included (complete medium, pH 7–7.2). Attached cells were resuspended in fresh complete medium by using a 14-gauge, 10-cm laboratory cannula (Becton Dickinson, Oxnard, Calif.) with bent tip fitted to a 5-ml LuerLok syringe. One-half of the cell suspension was transferred to a new 25-cm$^2$ flask and the medium volume in both the parent and the daughter cultures brought back to 6 ml. Subsequently, 2 subcultures were initiated from each parent culture by transferring one-third (equivalent to a subculture ratio of 1 to 5) of the cell suspension to a new flask, leaving approximately one-half in the parent culture. Cultures in which the cells multiplied to cover 90% or more of the culture substrate (confluency) within 2 weeks after subculturing were also subcultured and photographed using a inverted phase-contrast microscope.

Staining for Rickettsial Agents

To test cell lines for the presence of rickettsial agents, cell cultures were resuspended at a concentration of 5×10$^4$ cells/ml and 0.5-ml volumes centrifuged onto microscope slides using a Cytospin (Shandon Southern Instruments, Sewickley, Pa.) at 60 g for 10 min. The preparations were heat-fixed and immediately stained with Gimenez' (Stain Technology 39:135 1964) stain or fixed twice in absolute methanol and stained for 30 minutes at 37 C in 6% Giemsa's stain in Sorensen's phosphate buffer, pH 6.5. Stained slides were examined using a magnification of 1,000×.

For immunofluorescence microscopy, the slides were double fixed in methanol, overlaid with rabbit antiserum directed against spotted fever group rickettsiae (obtained from Dr. R. A. Heinzen, Rocky Mountain Laboratories, Hamilton, Mont.), diluted 100-fold in phosphate-buffered saline (PBS), pH 7.2, and incubated for 30 minutes at 37 C in a humid atmosphere. The preparations were then rinsed in sterile H$_2$O, immersed for 10 minutes in PBS with 3% bovine serum albumin (BSA), pH 7.2, and incubated for 30 minutes with fluorescein-isothiocyanate-labeled goat anti-rabbit IgG (Sigma, St. Louis, Mo.). The slides were rinsed in PBS, mounted in PBS with 3% BSA and 10% glycerol, and viewed under UV light illumination using a microscope equipped for epifluorescence.

Cryopreservation

From the first subculture, cell lines were periodically frozen in liquid nitrogen using a Union Carbide Freezing Tray (Indianapolis, Ind.) and a 35 VHC liquid nitrogen tank (Taylor Wharton Cryogenics, Theodore, Ala.). The setting of the device that yielded a temperature drop of 1° C. per minute was determined as follows: the level of nitrogen in the tank was measured from the center using a dip stick marked at 1-cm intervals. A small hole was drilled into the cap of a 1.8-ml capacity plastic freezing tube with "male" screw cap. The tube was filled with 1.5 ml of freezing medium (see below) and a thermocouple inserted through the cap into the medium. This and 5 additional tubes containing freezing medium were placed into the stage of the freezing tray adjusted to the highest position and inserted into the neck of the nitrogen tank. Every 10 minutes the temperature was recorded using a Bailey cryothermometer (Bailey Instruments Co., Saddle Brook, N.J.) until a temperature of −60° C. was reached. These measurements were repeated for each setting of the tray (settings 1–6) and for several levels of nitrogen in the tank (between approximately 15 cm and 30 cm). We noted that at about −25° C., i.e., 45 minutes after beginning the freezing process, a brief rise in temperature occurred; this was dampened by lowering the freezing stage by 2.5 cm at that time. The derived data were tabulated and used to determine the appropriate conditions for freezing cells.

For each 25-cm$^2$ flask of cells to be frozen, 1.5 ml of freezing medium was prepared by adding 10% dimethyl sulfoxide (DMSO) to complete medium with 20% FBS. When the exothermic reaction had subsided, the cultures were resuspended in freezing medium and 1.5 ml of cell suspension placed into freezing tubes. Tubes were evenly spaced in the freezing tray adjusted to a position appropriate for the amount of nitrogen and the number of tubes. After 45 minutes, the crank was turned to lower the stage by 2.5 cm.

The tubes were transferred into the liquid or vapor phase of nitrogen after a second period of at least 45 minutes. To test the viability of each batch, a tube of cells was regenerated after 1 week by quickly thawing it in a 37° C. water bath and adding the suspension to a 25-cm² flask in 5 ml of complete culture medium containing 50 μg gentamicin/ml. The following days, the supernatant was replaced with complete culture medium, and gentamicin was omitted after 1 week. Alternatively, freshly fed cultures could be held for several weeks to months at 12° C.

Karyotyping

To determine the diploid chromosome number for each cell line, cultures were treated overnight at 34° C. with 0.1 μg/ml of colcmid (GIBCO). The cells were then swelled in hypotonic saline, fixed in a mixture of glacial acetic acid and methanol, and dropped onto wet microscope slides (Nichols et al., Current Topics Microbiol Immunol. 55:61 (1971)). Chromosomes were stained in 10% Giemsa's stain and the modal number and distribution determined by evaluating 100 metaphase sets.

Isoelectric Focusing of Enzymes

Cells were washed twice in $Ca^{2+}$-, $Mg^{2+}$-free Dulbecco's phosphate-buffered saline (DPBS), resuspended in DPBS and centrifuged at 275 g at 4° C. for 10 minutes. The pellets were lysed in an equal volume of a 1% glycine solution and stored at −20° C. The internal organs from 5 unfed northern female *I. scapularis* ticks were pooled and extracted the same way. For comparison, extracts of line RAE25 (Munderloh and Kurtti, cited supra, 1989) from *R. appendiculatus* were run on the same gels. Extracts were clarified by centrifugation at 15,600 g for 15 minutes at 4° C. and were applied to squares of filter paper (5–10 μl/25 mm²) placed on the gel approximately 10 mm from the anode. Ampholytes (Ampholine® [pH 3.5–9.5] from Sigma or a mixtures of 3 ampholytes [pH 2.7–5, pH 5–7, and pH 8–10 [from BioRad, Hercules, Calif.) were incorporated into native polyacrylamide gels (8% total polyacrylamide concentration, with 3% bisacrylamide as the cross-linker) as directed by the manufacturer. Three isozymes were analyzed: lactate dehydrogenase (LDH, EC 1.1.1.27), malate dehydrogenase (MDH, EC 1.1.1.37), and malic enzyme (ME, EC 1.1.1.40). For LDH and MDH, Ampholine® (Sigma) was used, but the mixed ampholytes from BioRad were used to resolve ME. Bands were focused to equilibrium in a BioRad model 111 mini isoelectric focusing (IEF) cell at 4° C. in a 3-stage program for 15 minutes at 100 V, another 15 minutes at 200 V, followed by 450 V for 1 hour, as specified by the manufacturer.

Enzyme bands were visualized by incubating gels in the appropriate tetrazolium-based staining solution until bands were sufficiently developed as described by Pateur et al. Practical Isozyme Genetics, Ellis Horwood Ltd. (1988).

For LDH staining, the gels were incubated in the dark in a solution containing 1 ml of nicotinamide adenine dinucleotide (NAD+, 1% in $H_2O$), 6 ml of 0.5M lithium D-L-lactate, and 35 ml of 0.2M tris(hydroxymethyl) aminomethane HCL, pH=8 (TRIS-A). Just before use, a 1% aqueous solution of nitroblue tetrazolium (NBT, 0.3 ml) and a 1% aqueous solution of phenazine methosulfate (PMS) were added. When dark blue bands appeared, the gels were washed in deionized water and fixed in absolute methanol.

For MDH staining, the gels were immersed in a solution made of 2 ml NAD+ (1%), 0.3 ml 0.5M $MgCl_2$, 5 ml 2M malic acid (pH=7), and 35 ml TRIS-A. Nitroblue tetrazolium (0.3 ml) and 0.5 ml PMS were added immediately prior to use. The gels were incubated for 30–60 minutes in the dark until dark blue band appeared, then washed and fixed as stated for LDH.

To stain ME, the following components were mixed together: 0.1 ml nicotinamide adenine dinucleotide phosphate (NADP+), 1 ml 2M malic acid (pH=7), 1.5 ml 0. 5M $MaCl_2$, and 10 ml TRIS-A. Phenazine methosulfate (0.1 ml, 1%), 0.3 ml NBT (1%), and thiazolyl blue (MTT, 1%) were added freshly. This solution was brushed on to the gel and the gel incubated in the dark for 30–60 minutes. It was washed and fixed as stated above. The distance of migration of isozyme bands in air dried gels was measured from the anode.

Eight proteins with known isoelectric point (pI) values ranging from 4.65 to 9.6 (BioRad) were resolved under nondenaturing conditions in polyacrylamide gels as described above using Sigma's ampholine (range 3.5–10) or the ampholyte mixture from BioRad. The running conditions were identical to those used for cell extracts. The gels were fixed and stained with BioRad's silver stain kit. To determine the pI values of unknown isozymes, bands in cell extracts were compared with the known protein in a "standard" gel employing the appropriate ampholyte. Extracts from cell lines (kept separate by subculture number) or female ticks were run at least 3 times in different gels and the values calculated for each band were averaged.

Results

The egg masses from feral northern black-legged ticks weighed 77 mg on average (range: 19–147 mg) and those from southern females ranged from 59 mg to 147 mg with an average weight of 102 mg. The embryos were used at an age of 23–27 days po. All cultures from egg masses of feral ticks remained clean, but 10 of 17 from laboratory-raised females became contaminated within 10 days with antibiotic-resistant bacteria. Contaminated cultures were discarded. All feral egg masses were fertile, but 1 of the laboratory-raised females laid an unfertilized batch of eggs weighing 122 mg. Only egg masses that weighed at least 90 mg gave rise to successful primary cultures with the exception of 1 egg mass weighing 66 mg (embryo age: 25 days po). Cultures with low cell numbers could be "rescued" by pooling cells from 2 to 6 flasks as appropriate. Cells in pooled cultures subsequently resumed growth and developed into established lines.

Attachment of single, hemocyte-like cells was detected within several hours of seeding. Fragments of gut and Malpighian tubules were recognized by their microscopic appearance, active contractility, and the presence of guanine granules in the latter. Leg fragments were identifiable by the presence of epidermal structures such as cuticle and claws. Central ganglia with nerve trunks attached were present as well. These tissues remained nonadherent at first but later, within a week to a month, became anchored to the culture substrate with cells migrating from the torn or broken ends. Multicellular, hollow spheres (vesicles) frequently grew from hollow organs from which they eventually detached. Such structures (i.e., vesicles) have been described in many invertebrate cell lines.

The time interval between initiation of the primary culture and when the first subculture was made ranged from about 6 months to 12 months. Cultures from large inocula resulted in a more diverse mixture of cells than those that were seeded with tissues from fewer eggs, or with the egg shell fraction. Line IDE1 grew loosely attached to the substrate as clumps of small round cells mixed with a few larger ones. Line IDE2 contained firmly adherent cells as well as others that were refractive and round. Line IDE8 cells characteristically had very long (30–40 μm or more), often branching, pseudopodia and resembled neuronal cells. IDE12 cells had the appearance of plasmatocytes in Wright-stained smears.

Cell line ISE5 contained the most diverse cell types. Long, bipolar cells with a foamy cytoplasm were common and grew between clumps of round cells and adherent vesicles. While myoblasts were present in all young lines, pulsating myotube-like structures were more common in ISE5. Line ISE18 cells also tended to form muscle, but here large patches of flattened cells twitched and shifted in an unorganized fashion. ISE6 cells are round or spindle shaped and often grow in multilayered clusters surrounded by individual cells. Differentiated muscle tissue rarely formed in more highly passaged cell lines (>10 subcultures). With subculturing, the number and diversity of cell types in a line declined, and 1 or 2 cell types became dominant. This was shown by comparing the longer-established IDE lines, particularly IDE1, with the younger ISE lines. Attempts to clone any tick cell lines either by limiting dilution or soft-agar cloning were unsuccessful. Subcultures were done every 2–4 weeks by diluting the cell suspension 5–10-fold. The cells reattached within a few hours of postseeding.

Two representative electron micrographs are shown in FIG. 1. In FIG. 1A, an electron micrograph of cell line IDE8 is shown. The IDE8 cells have characteristic stacks of fine wavy material resembling strands of hair. In FIG. 1B, an electron micrograph of cell line ISE6 is seen. The ISE6 cells are typically found in close association with one another.

Cells thawed from liquid nitrogen storage were successfully re-established in culture.

We found no evidence for the presence of rickettsial agents in the cell lines by staining with Giemsa's or Gimenez' cited supra (1964) stain, or by indirect immunofluorescent antibody testing.

Figure 2:
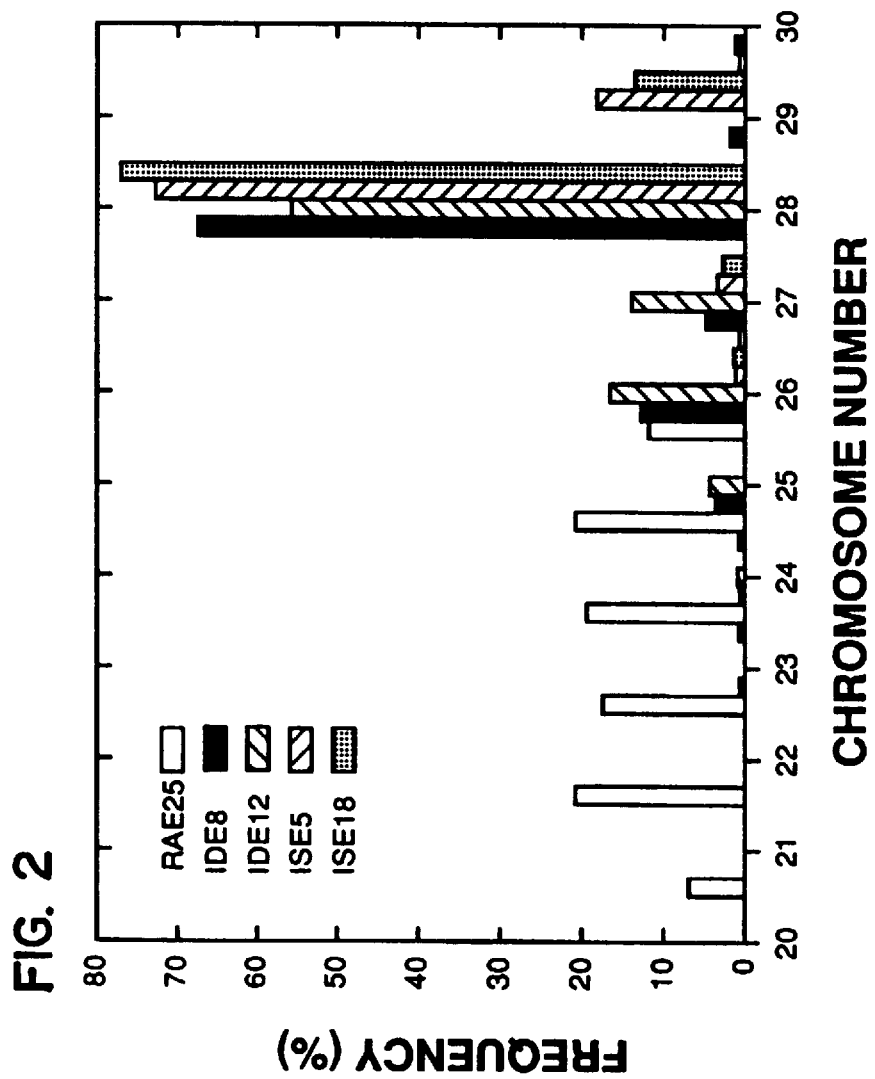
FIG. 2. Karyotypes of *Ixodes scapularis* cell lines IDE8 and 12 and ISE5 and 18 compared with the karyotype of a long-established cell line from the tick *Rhipicephalus appendiculatus*, RAE25. Cells, passages 6–31, were treated with colcemid overnight and the modal number of distribution of Giemsa-stained chromosomes determined by evaluating 100 metaphase sets.

All cell lines were predominantly diploid (FIG. 2) and the modal number of chromosomes (28) and their general morphology conformed to that reported for *I. scapularis* by Oliver et al., *Journal of Medical Ent.* 30:54 (1993). By comparison, the highly passaged cell line RAE25 had about equal numbers of sets with 22–25 chromosomes and approximately 10% of the sets had 21 and 26 chromosomes, respectively. *Rhipicephalus appendiculatus* has an XX/XO sex-determining system with 2n=22 in female and 21 in male ticks (Wysoki and Bolland, Genetica 48:233 (1978)).

Figure 3:
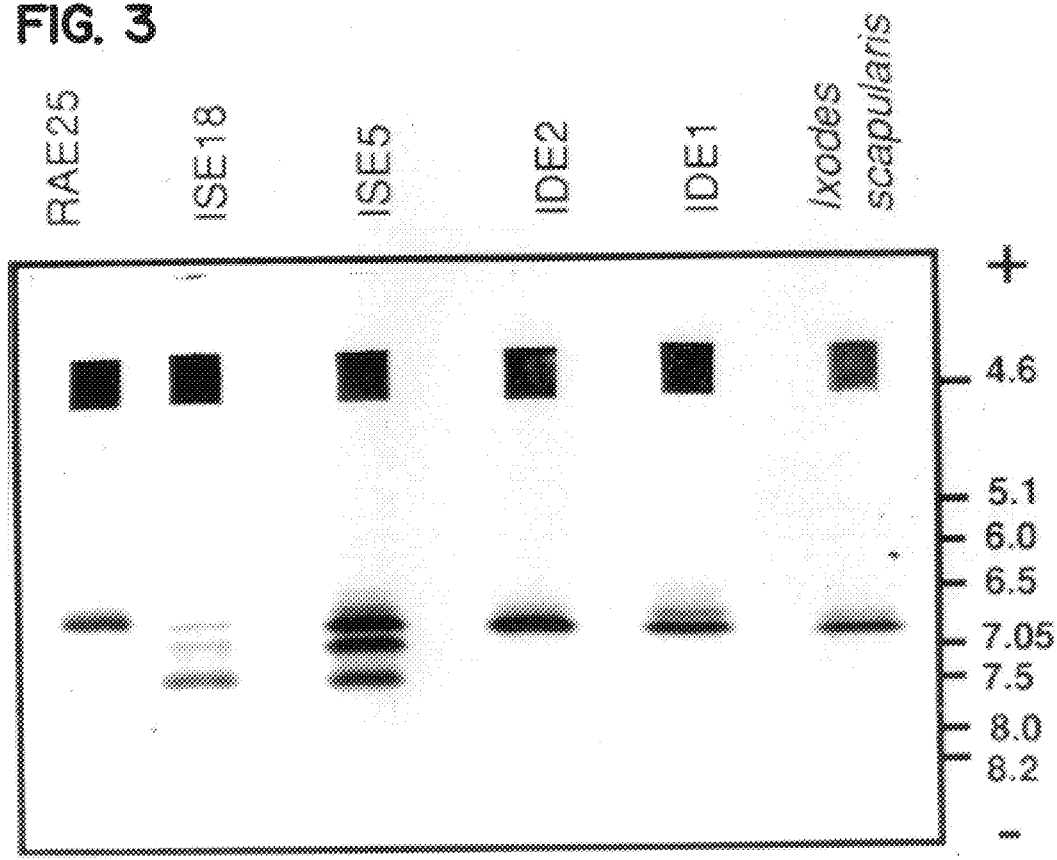
FIG. 3. Isoelectric focusing pattern of lactate dehydrogenase (LDH) in *Ixodes scapularis* cell lines and tissue extracts from *I. scapularis* females compared with cell line RAE25 isolated from the tick *Rhipicephalus appendiculatus*. The pI values of standard enzymes are indicated on the right margin between the panels. +, position of the anode and −, position of the cathode.

Lactate dehydrogenase (FIG. 3) was readily stainable in extracts from all cell lines. All IDE lines showed 1 major band with a pI value of 6.8. In line ISE5, there were 2 additional, consistent major bands with pI values of 7.0 and 7.5, respectively. In ISE18, the same 3 bands were present in early subculture (<10) cell extracts; but, in cells that had been in culture longer, the 2 bands with the lower pIs diminished in intensity, leaving only the isozyme with a pI of 7.5. Extracts from tick tissues displayed a single major band that corresponded to that in the majority of the cell lines (pI=6.8). RAE25 cells also had only 1 band that consistently focused at a slightly more acidic pH (pI=6.7) than IDE and ISE extracts.

Figure 4:
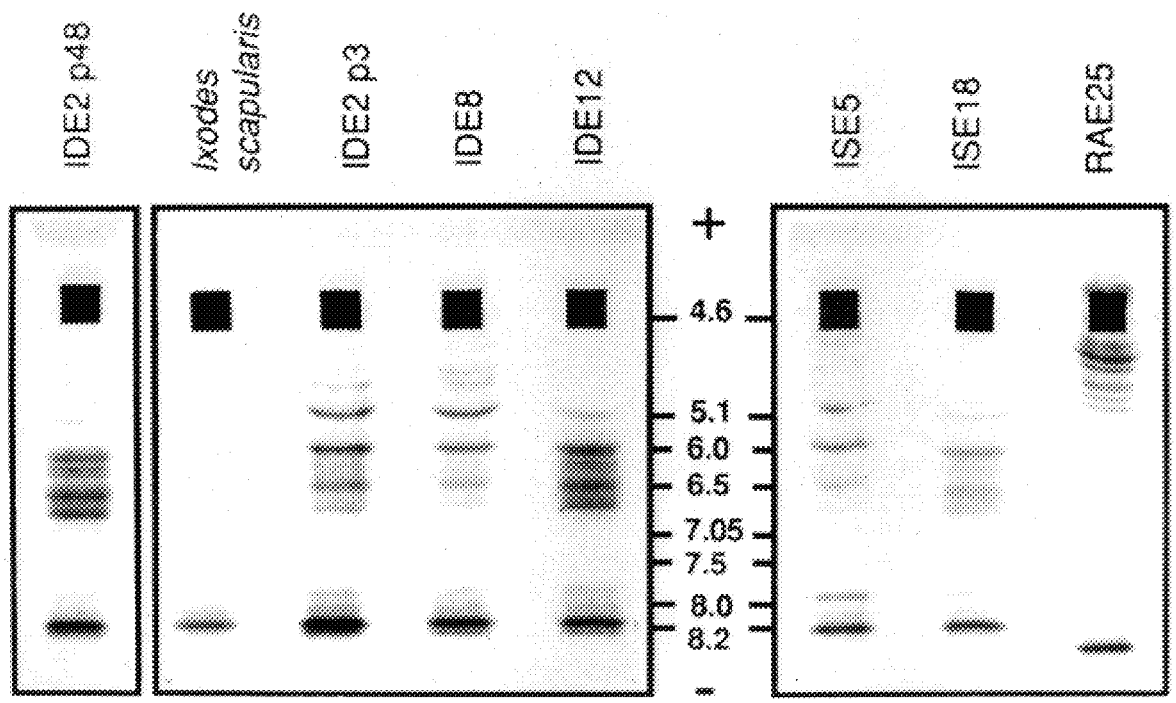
FIG. 4. Isoelectric focusing pattern of malate dehydrogenase (MDH) in *Ixodes scapularis* cell lines and tissue extracts from *I. scapularis* females compared with cell line RAE25 isolated from the tick *Rhipicephalus appendiculatus*. Samples in different panels were run in different gels. The pI values of standard enzymes are indicated on the margins between the panels. Note diminishing intensity of the isozyme band with a pI value of 5.1 in cell line IDE2 passage (p) 48 as compared with that band in IDE2 p3. +, position of the anode and −, position of the cathode.

In Ixodes cell lines and extracts from female northern black-legged ticks the MDH staining pattern was more complex (FIG. 4). The most prominent band was an enzyme focusing at pH 8.5. This was accompanied by a minor band equilibriating at pH 8.1, which was very intense in ISE5. In addition, there were 4 lesser bands with mildly acidic to neutral pI values of 5.1, 6.1, 6.7, and 6.9. The last band was distinct in IDE12 and IDE2 but weak in the other cell lines, whereas at higher passage numbers (>30) the isozyme band with a pI value of 5.1 diminished. In comparison, the *R. appendiculatus* line RAE25 had 1 enzyme species with a pI value near 9 and 4–5 inconsistent minor bands with pIs between 4 and 5.

In Ixodes cells, the ME (FIG. 5) staining pattern did not include any alkaline isozymes and all bands focused between pH 5.0 and 6.5. There were 3 major bands that focused at pH 6.2, 6.4, and 6.5. In addition, there was a weak but consistent band with a pI value of 5.1 followed by two stronger isozymes with pIs of 5.3 and 5.6, which were most evident in ISE18 and less intense in IDE12 and 2. Tick tissue extracts had rather weak ME activity, showing the major band at ph 6.0 and a minor band at 5.1. RAE25 cells displayed a major band that focused at pH 6.5, followed by 1 or 2 bands with pI values of 6.7 and 6.8. An additional minor but distinct isozyme focused at pH 5.5.

LDH, MDH and ME yielded the most consistent results. The pattern of minor and major MDH bands allowed distinction between the genera Ixodes and Rhipicephalus, but not between Ixodes lines. Lactate dehydrogenase gave the most consistent banding pattern and discriminated between IDE lines and ISE5 and ISE18. In other species, e.g., mosquitoes, LDH is known to be a tetramer and must be in its tetrameric form in order to function (Pasteur et al., cited supra 1988). The fact that ISE5 showed 3 major LDH bands and most other Ixodes cell lines showed 1 band may indicate that in *I. scapularis* LDH is a dimer. We found both dehydrogenases useful for distinguishing Ixodes cell lines from cell line RAE25. Although ME showed a similar pattern in all cell lines examined, 2 distinct minor bands (pI of 6.7 and 6.8) were found only in RAE25. Degradation of $NADP^+$ can generate enough $NAD^+$ to reveal MDH activity in gels stained for ME. Thus, it is conceivable that those bands in the ME gels that focused at a similar pH as some of the MDH bands actually represented MDH. However, a band analogous to the most intensely staining MDH band with a pI of 8.5 never appeared in ME gels, arguing against $NAD^+$ contamination. Furthermore, $NADP^+$ was either prepared fresh or stored frozen to guard against degradation. The enzyme activities and banding patters of the Ixodes cell lines were consistent with the data obtained from tick tissue extracts, confirming their species identity. While karyotype analyses also confirmed the cell lines to be of Ixodes origin, this technique did not detect differences between cell lines.

Tick cell culture IDE8 was deposited with the American Type Culture Collection in Rockville, Md. Tick cell culture IDE8 has the following characteristics: The cells grow firmly attached to the substrate with a population doubling time of approximately 6 days. They are primarily round, particularly at high cell density, but may form long pseudopodia. A unique ultrastructural feature are folded membrane stacks with vacuoles. The modal chromosome number is 2n=28 with two sex chromosomes. An electron micrograph of tick cell culture IDE8 is shown in FIG. 1A. The tick cell culture has been given Accession No. CRL 11973.

The tick cell culture ISE6 has been deposited with the American Type Culture Collection in Rockville, Md. The characteristics of ISE6 are: These cells are much less firmly attached and spindle-shaped. They grow at the same rate as IDE8 cells and share the same chromosome complement of 2==28 with two sex chromosomes. An electron micrograph of ISE6 cells is shown in FIG. 1B. The tick cell culture has been given Accession No. CRL 11974.

The tick cell cultures isolated from *Ixodes scapularis* represent undifferentiated cells that did not display specific functions except the formation of muscle. After several passages, most cultures contain one or two types of cells. The cell lines were not contaminated with symbiotic or pathogenic rickettsial agents or viruses. Examination of the cells by electron microscope did not reveal any contamination with rickettsial agents, and viruses.

EXAMPLE 2

Infection of Tick Cell Culture with *Anaplasma marginale*

An established tick cell line derived from *Ixodes scapularis* was infected with erythrocytic stages of *A. marginale*. Development of the rickettsia into colonies similar to those found in naturally-infected ticks was seen in tick cell cultures.

Infected bovine blood was used as the inoculum. Venous blood infected with the Virginia isolate of *A. marginale* (parasitemia 30%), was collected from calf PA291 (in Vacutainer® tubes with citrate as anticoagulant and frozen). The blood was mixed with 10% v/v dimethyl sulfoxide (DMSO), frozen at a rate of −1° C./minute and stored in liquid nitrogen in 1.5 ml aliquots. Established cell lines from three genera of ticks (Dermacentor, Ixodes and Rhipicephalus) were inoculated with thawed blood stabilate. Two cell lines derived from ticks known to transmit *A. marginale* in nature, *D. variabilis* and *D. albipictus*, and one from the phylogenetically primitive genus Ixodes (cell line IDE8 from *I. scapularis*). Cell lines were maintained in L-15B medium as described by Munderloh and Kurtti 1989 cited supra. Antibiotics were not used in the cultures as they might interfere with cell to cell spread of the organisms. The addition of $NaHCO_3$ and MOPS to the culture medium was important because without $NaHCO_3$ the organisms did not multiply.

A 25-cm² flask of a confluent tick cell culture, one from each cell line, was inoculated with the contents from one freezing tube (1.5 ml) which had been thawed quickly by immersion into a water bath, causing lysis of the red blood cells (RBC). Cultures were incubated overnight at 34° C. in 5 ml per flask of tick cell culture medium, pH 7.2, additionally supplemented with 0.25% $NaHCO_3$ and 10 mM of an organic buffer, 3-(N-Morpholino) propanesulfonic acid (MOPS) (Anaplasma medium). The next morning, cultures were mixed with fresh, uninfected tick cells from the same cell line to replace those that had lysed, probably due to the high level of hemoglobin. The suspensions were centrifuged at 2000×g for 60 minutes to force liberated rickettsiae into tight contact with tick cells. The pellets were resuspended in fresh Anaplasma medium and returned to the flasks. Residual RBC ghosts were gradually removed during medium changes. Subsequently, the Anaplasma medium in infected cultures was replaced once a week. When desired, a sample of 0.2 ml was taken at that time by resuspending the entire culture. Cell spreads were prepared and stained with Giemsa's stain as described [T. J. Kurtti, S. E. Ross, Y. Liu, & U. G. Munderloh, *J. Inverebr. Pathol.* 63:188 (1994)].

Cell line IDE8 became infected with *A. marginale*, and the isolate, named Am291, was continuously maintained in this cell line for 14 serial passages during 16 months. Replication of *A. marginale* in IDE8 cells was first discovered 34 days post inoculation (pI) by light microscopic examination of a stained cell sample. At that time 30% of the cells appeared infected, although a cytopathic effect (CPE) was not seen by phase contrast microscopy. Lack of CPE continued to be a feature of infected cultures until the 5th passage.

Identity of the parasite was confirmed using a specific DNA probe and the standard polymerase chain reaction (PCR). Infected cells strongly hybridized with a probe specific for *A. marginale*, and *A. marginale* specific oligonucleotide primers amplified a single product of the expected size (FIG. 6).

The specific DNA probe was made by amplifying a 409-bp fragment of the *A. marginale* msp 1β gene (A. F. Barbet, A. R. Alfred, *Infect. Immun.* 59,971; 1991) using primers BAP-2 (GTA TGG CAC GTA GTC TTG GGA TCA and AL34S (CAG CAG CAG CAA GAC CTT CA) (R. W. Stich, J. A. Bantle, K. M. Kocan, A. Fekete, *J. Med. Ent.* 30, 781; 1993). The probe was labeled by incorporation of digoxigenin-labeled nucleotides (11-dUTP) during PCR. DNA was amplified and simultaneously labeled in 100 μl reactions comprising 1.25 units Taq DNA polymerase, 1 μM of each primer, 1 ng of *A. marginale* DNA purified from erythrocytes, 0.2 mM of dCTP, dATP and dGTP, 0.13 mM of dTTP and 0.03 mM of digoxygenin-11-dUTP. The buffer was 1.5 mM $MgCl_2$ and 50 mM KCl in 10 mM Tris-HCl pH 8.3. Amplification was performed for 35 cycles of 95° C. for 1.5 min, 57° C. for 2 min and 72° C. for 3 min. The probe was purified by ethanol precipitation.

For slot blot hybridization, total DNA from infected IDE8 tick cell cultures was extracted with phenol/chloroform/isoamyl and precipitated with Na-acetate and ethanol following standard procedures (Sambrook, J., Fritsch, E. F. and Maniatis, T. 1989. Molecular Cloning, A. Laboratory Manual. Cold Spring Harbor Laboratory Press). Extracts were diluted serially 2-fold, and transferred to a nylon membrane using a slot blot apparatus. Infected and uninfected erythrocytes as well as uninfected host cells (IDE8) were processed the same way as positive and negative controls. The probe has previously been proven to specifically detect only *A. marginale* DNA. FIG. 6A shows that the probe detected *A. marginale* DNA in infected erythrocytes (the positive control) and in infected tick cell cultures, but not in the negative controls (uninfected erythrocytes and uninfected IDE8 cells).

Hybridization conditions for slot blot hybridization are: treated DNA samples bound to nylon membranes were treated with a prehybridization solution containing sarkosyl and salmon sperm DNA. After blocking, the membranes are soaked in a hybridization solution including 30 ng/sq. cm. of membrane of digoxigenin labelled probe. After an overnight exposure, the membranes are washed 4 times in SSC at 68° C. Hybrid formation is detected with alkaline phosphatase conjugated anti-digoxigenin antibody and substrates 5-bromo-chloro-3-indolyl phosphate and nitroblue tetrazolium salt.

PCR using infected tick cell culture extract as a template further confirmed the identity of the Anaplasma growing in IDE8 cells. A crude lysate was made according to Higuchi (Higuchi, R. 1989. Rapid sample preparation for PCR. In *PCR Technology, Principles and Applications for DNA Amplification*, H. A. Ehrlich, Ed. (Stockton Press, N.Y., 1989), chap. 4. Briefly, infected tick cells from one culture were forced ~10 times through a 27 gauge needle, and large debris removed by centrifugation at 100 g. The supernatant fluid containing small particles and Anaplasma was collected by centrifugation at 10,000 g for 20 min, and the pellet resuspended in lysis buffer with, NP-40, Tween-20 and Proteinase K (Higuchi 1989). Following incubation at 55° C. for 1 hr, the proteinase was inactivated (95° C. for 20 min), and the lysate stored at −20° C. Uninfected IDE8 cells were extracted the same way as a control. 3–5 μl of this lysate were used as a template in the PCR with primers BAP-2 and A134S at a concentration of 0.5 μM each. 100 μl reaction mixtures containing 1.5 mM MgCl2 and 0.2 mM of the four deoxynucleotides were cycled 30 times through 94° C. for 1 min, 60° C. for 1 min and 72° C. for 30 sec, followed by a final extension period of 3 min at 72° C. 10 μl of the resulting DNA was mixed with loading buffer (Ficoll 400 with bromophenol blue) and electrophoresed through 1% agarose in 0.5×TBE (tris-borate-EDTA) buffer for 1.5 hr at 100 Volts (Sambrook et al., 1989). The gel was subsequently stained with ethidium bromide and photographed under UV light. (See FIG. 6B) Lysate from infected IDE8 cultures gave rise to a DNA product of the expected size, 409-bp, while control lysate did not.

*A. marginale* was propagated both by adding infected cells to uninfected ones at ratios of 1 to 3 or up to 1 to 20, and by diluting an infected culture into 2 or 3 flasks without adding uninfected cells. At first, rickettsial multiplication and cross-infection of tick host cells was slow, and the highest levels of infection were seen in chronically infected cultures (up to 60%) 5 months pI. With continuing passage, Am291 became better adapted, and cultures diluted 1 to 20 with uninfected cells were nearly 100% infected in 3 weeks. The organisms multiplied more rapidly, producing large colonies that cause degeneration of heavily infected cells. Because individual colonies of *A. marginale* in IDE8 cells grow to considerable size, often larger than the host cell nucleus, and may contain hundreds of rickettsiae, one 25-cm$^2$ flask containing 5 ml can supply many more organisms than an equal volume of highly infected RBCs which contain inclusion bodies with only 4–8 rickettsiae.

*Anaplasma marginale*-infected IDE8 cells were successfully frozen under controlled conditions as described in Example 1, and stored in liquid nitrogen as early as the second passage in vitro.

Infected cells from one 25-cm$^2$ culture were suspended in 4.5 ml L-15B medium containing 20% fetal bovine serum and 10% DMSO and dispensed into 3 freezing vials. They were frozen under controlled conditions. To regenerate a culture, the thawed cell suspension was centrifuged for 15 minutes at 15,000 g and the pellet of infected cells and rickettsiae introduced into a new IDE8 culture with Anaplasma medium.

Figure 7A:
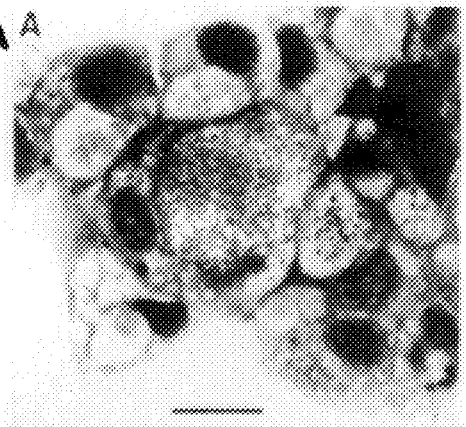
FIG. 7. Appearance of *Anaplasma marginale* in tick cells cultured in vitro. 7A. Giemsa-stained smear of an *A. marginale*-infected culture, cell line IDE8, derived from embryos of the black-legged tick, *Ixodes scapularis*. *A. marginale* had been serially passaged 6 times in this cell line. At the time the culture was sampled, 74% of the tick cells were infected. Note that the endosomes are more or less densely filled with rickettsiae. Bar represents 10 μm. 7B. Electron microscopic appearance of *A. marginale* passaged twice in IDE8 tick cells. Infected IDE8 cells were centrifuged at 150 g for 10 minutes, and the pellet flooded twice with ice cold glutaraldehyde in cacodylate buffer. One large and one small colony occupy the same host cell, indicating multiple invasion events. The larger colony contains a mixture of dense and reticulated rickettsial forms. Bar represents 4μm. 7C. Higher magnification of small colonies containing reticulated forms of *A. marginale* passaged 4 times in vitro. Bar represents 1 μm.
Figure 7B:
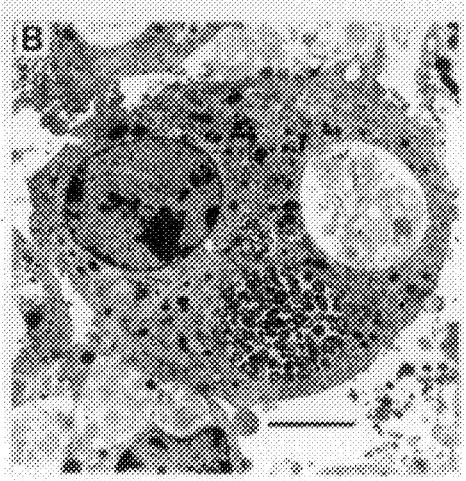
Figure 7C:
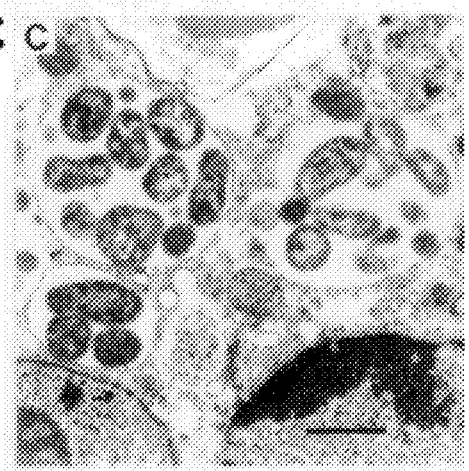

Initially, the morphology of *A. marginale* in cultured tick cells was not typical of those ticks or cattle. Rather, they appeared highly pleomorphic by transmission electron microscopy with only a few in each host cell endosome (not shown). In continuous culture the infection of an IDE8 cell begins with an electron dense form of the rickettsia (measuring approximately 0.5–0.6 μm in diameter) binds to a tick cell at multiple sites. This contact initiates the host cell envelopment of the rickettsia by endocytosis. Within a vacuole of host cell origin the rickettsia undergoes binary fission into reticulated forms. Continued division results in colonies of 12 μm or larger containing many organisms. In some colonies large reticulated forms of 3–4 μm in diameter are seen. In developing colonies reticulated forms are irregular in shape and size. In mature colonies rickettsiae appear rounded and contain many dense forms which are released from the host cell without apparent damage to the host cell. As infection develops within the monolayer multiply-infected host cells are found. In monolayers with a high % of infected cells the density of rickettsiae appears to overwhelm the host cell resulting in death and the rupturing of the cells. This results in progressive focal detachment of the monolayer. Cultures contain a mixture of dense and reticulated forms at this point. With continued cultivation typical electron-dense and reticulated forms predominated in the culture, and the number of organisms in each endosome increased (FIG. 7). These dense colonies were similar to those described in midgut, gut muscle and salivary gland cells of naturally-infected ticks (Kocan et al., *Am. J. Vet. Res.* 53:499 (1992)).

*A. marginale* was also propagated in ISE6 cells. ISE6 cells were grown and infected with *A. marginale*. In cell line ISE6, *A. marginale* grew essentially the same way as it did in IDE8 cells. ISE6 cultures were initially infected using infected IDE8 cells, and then serially passaged 4 times by diluting infected with uninfected ISE6 cells 10 fold every 4 weeks. In these cultures, up to 70% of cells became infected as judged by Giemsa-stained smears. Development of *A. marginale* was similar, and cells contained both parasitophorous vacuoles filled with just a few rickettsiae and vacuoles densely packed with large numbers of *A. marginale*.

For the first time *A. marginale* was grown in vitro in tick cells where the organisms multiplied into colonies typical of those found in ticks, and cross-infected nearly 100% of the host cell population. Although cell line IDE8 was not derived from a known vector of *A. marginale*, it apparently provided an appropriate environment for rickettsial growth and development. In contrast, cell line DALBE3 from a natural vector (*Dermacentor albipictus*) does not support growth of *A. marginale*. Culture derived *A. marginale* can provide a source of antigen free of RBCs and at a much higher concentration.

*A. marginale* grown in tick cell cultures is essentially free of bovine red blood cell contamination and bovine pathogens. Because the *A. marginale* is passaged at least twice over a period of about 6 to 8 weeks any bovine erythrocyte contamination from the inoculum is removed. Electron micrographs *A. marginale* infected tick cell culture indicate no contamination with bovine red blood cells or pathogens. The only possible source of contamination with either bovine red blood cells or pathogens is the fetal bovine serum or bovine lipoprotein used in the media. The fetal bovine serum used is filtered through 0.1 μm filter and should be free of bovine erythrocytes and bovine pathogens. The bovine lipoprotein is filtered with 0.2 μm membrane filters.

EXAMPLE 3

Infectivity of *Anaplasma marginale* Grown in Tick Cell Cultures

*A. marginale* grown in IDE8 tick cell cultures retained infectivity for cattle. The contents from two cultures, in which 61% and 57%, respectively, of the cells were infected was collected. *Anaplasma marginale* had been passaged in 1 culture 2 times and in the other culture 4 times as shown in Table 1. This inoculum was inoculated intravenously into two splenectomized, 3 month-old calves PA344 and PA346. Both developed clinical anaplasmosis.

Laboratory-reared, uninfected male *D. andersoni* that fed on the calves subsequently transmitted *A. marginale* during transmission feeding on a susceptible calf (Table 1). Light microscopy and slot blot analysis indicated that approximately 95% of the ticks had acquired the rickettsiae (data not shown).

TABLE 1

Infectivity of *Anaplasma marginale* grown in tick cell culture. Two splenectomized Hereford calves (PA344 and PA346, 3 months old) were injected intravenously with the contents (infected tick cells and supernatant culture medium, 5 ml) of one 25-cm² flask each. Both calves recovered to become chronic *Anaplasma marginale* carriers. Calf PA343 (not splenectomized, 3 months) was infested for 10 days with 400 male *Dermacentor andersoni* ticks (95% of ticks infected) that had fed on PA344 for 10 days during the 3rd to 4th week pI.

| Animal # | Time in Vitro/Passage | Prepatent Period | Max. Parasit. | % > in PCV[1] |
|---|---|---|---|---|
| PA344 | 5 mos/Passage 2 | 15 days | 52% | 66% |
| PA346 | 9.5 mos/Passage 4 | 26 days | 44% | 77% |
| PA343 | tick transmission from PA344 | 21 days | 7% | 34% |

[1]packed cell volume

These results indicate that *Anaplasma marginale* grown in tick cell culture retains infectivity for cattle. Culture grown *Anaplasma marginale* was also transmitted from infected animals to another animal.

EXAMPLE 4

Antibody Reactivity with *Anaplasma marginale* Grown in Ixodes Cell Culture

*Anaplasma marginale* antigens were analyzed by western blot using serum from a cow hyperimmunized against the erythrocytic stages of *Anaplasma marginale*. This hyperimmune serum was prepared by Dr. Katherine Kocan and Dr. Edmour Blouin (Oklahoma State University, Stillwater, Okla.) using standard methods. Antisera was also obtained from an animal infected with *A. marginale* grown in tick cell culture as described in Example 3. Antigen was prepared from infected *Ixodes scapularis* cell culture (cell line IDE8), from infected salivary glands of the natural vector tick, *Dermacentor andersoni*, and from the infected bovine blood. Uninfected IDE8 cells and uninfected tick salivary glands (from *D. andersoni*) were used as controls.

Infected or uninfected cells or tissues were centrifuged into a pellet and extracted in four volumes of sample buffer containing 0.125M Tris-HCl pH 6.8, 2% Na-dodecylsulfate (SDS), 10% glycerol, 5% 2-mercaptoethanol, and 0.00125% bromophenol blue, and stored frozen. 5 microliters of samples, diluted further 5-fold in sample buffer, were separated by SDS polyacrylamide gel (10% acrylamide) electrophoresis according to the method of Laemmli (1970; Nature 227:680), and then transferred to Millipore Immobilon-P membranes.

Figure 8:
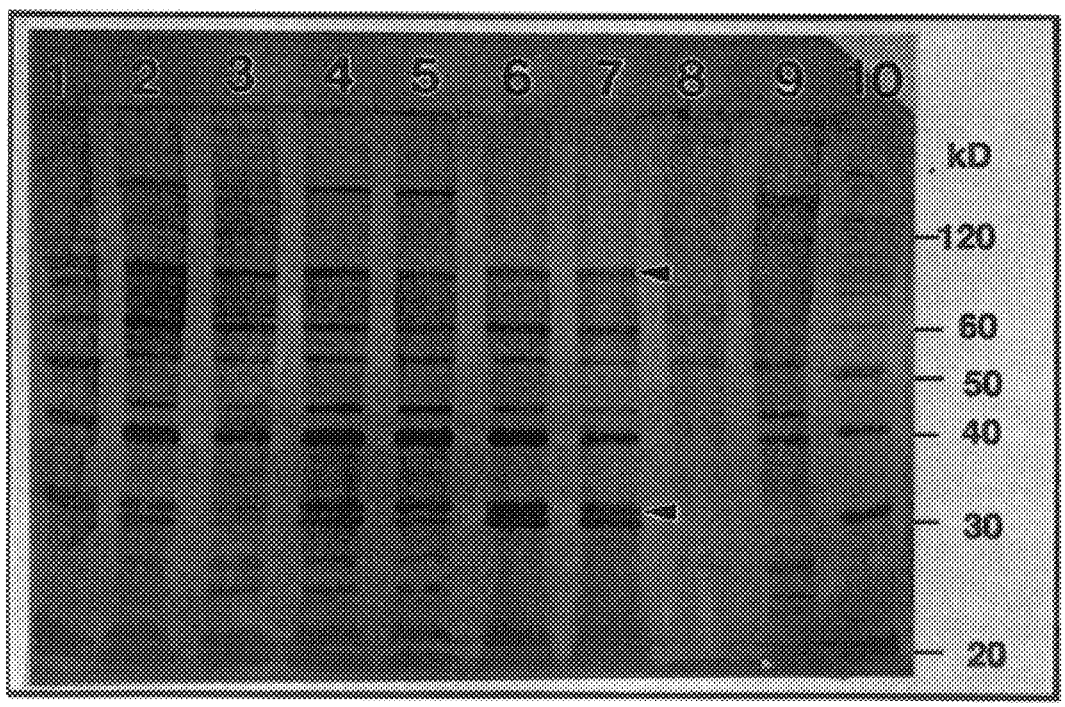
FIG. 8. Western blot showing antigenic profile of *Anaplasma marginale* from tick cell culture. Lanes 1 and 10: molecular weight markers. Lanes 2–7: infected cells. Lanes 8 and 9: uninfected cells.
Figure 9:
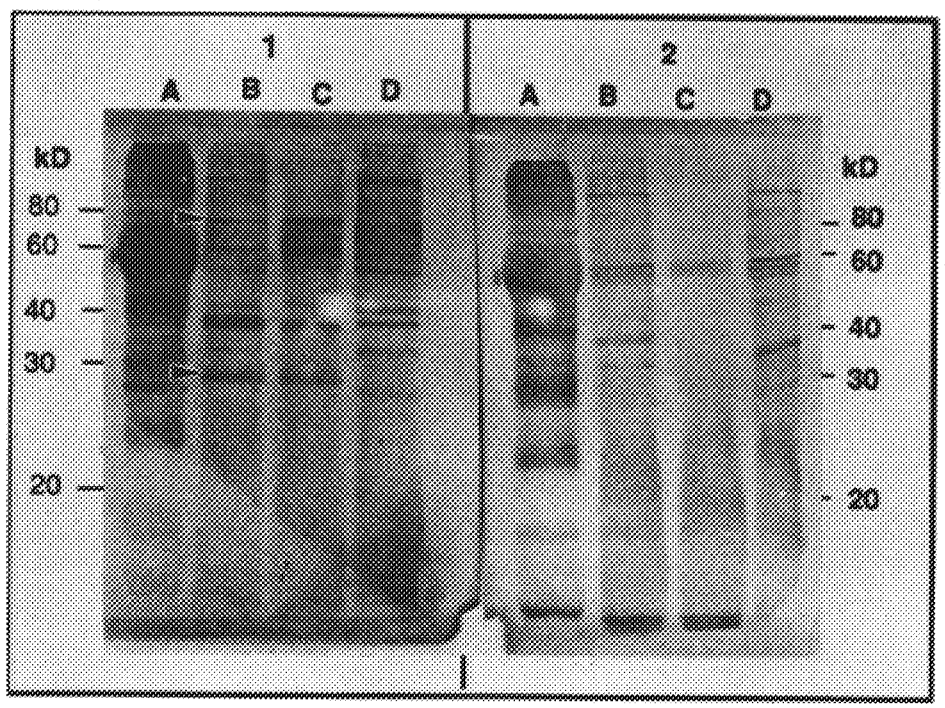
FIG. 9. Western blot comparison of antigenic profile of *Anaplasma marginale* infected erythrocytes and tick cell culture. Panel 1: antiserum from hyperimmune animal. Panel 2: antiserum from animal infected with *A. marginale* from tick cell culture. Lanes A: *A. marginale* infected bovine erythrocytes. Lanes B: tick cell line IDE8 infected with *A. marginale*. Lanes C: tick cell free supernatant from *A. marginale* infected IDE8 culture. Lanes D: uninfected IDE8 cells.
Figure 10:
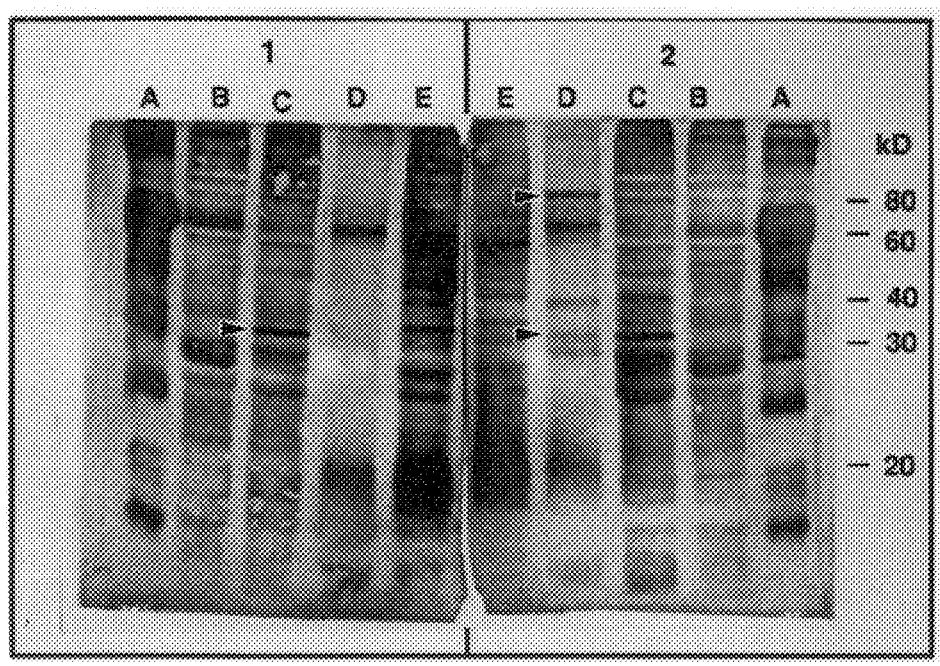
FIG. 10. Western blot comparison of antigenic profile of *Anaplasma marginale* infected erythrocytes, tick salivary glands and tick cell culture. Panel 1: antiserum from animal infected with *A. marginale* from tick cell culture. Panel 2: antiserum from hyperimmune animal. Lanes A: *A. marginale* infected bovine erythrocytes. Lanes B: uninfected tick, *Dermacentor andersoni*, salivary gland extract. Lanes C: tick, *D. andersoni*, salivary gland infected with *A. marginale*. Lanes D: tick cell line IDE8 infected with *A. marginale*. Lanes E: uninfected IDE8 cells.
Figure 12:
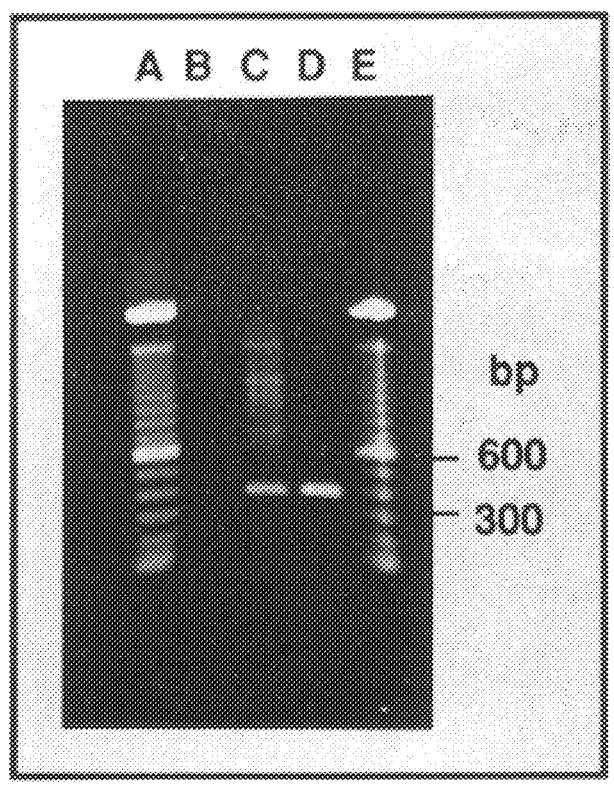
FIG. 12. PCR of *E. canis* and *A. marginale* grown in IDE8 cell culture. The primers are specific for each template DNA, but cycle conditions were optimized for *E. canis*, resulting in some non-specific amplification for *A. marginale*. *E. canis* primers used were those designed by Dr. George Murphy of Oklahoma State University, ECAN5 and ESPEC3, and those for *A. marginale* were BAP-2 and AL34S as described below. DNA was amplified during 30 cycles of denaturing for 45 sec. at 94° C., annealing for 30 sec. at 55° C., and extension for 90 sec. at 72° C. A single final extension cycle at 72° C. for 10 min. concluded the program. For both templates, the expected size of the amplicon is ~400 bp.

The results are shown in FIGS. 8, 9, and 10. In FIG. 8, antigens from *A. marginale* infected IDE8 cultures were obtained after 4 to 6 passages and stained with hyperimmune serum from calf PA200. *A. marginale* from infected tick cell cultures (lanes 2–7) have an 80 kDa band and a doublet at 30 kDa that are clearly associated with *A. marginale*. These antigens are also seen in *A. marginale* obtained from infected bovine erythrocytes. See FIG. 9, Lane A.

In infected bovine blood, the antibody recognized several bands with apparent molecular weights between 25 and 95 kDa (25, 28, 39, 41, two prominent bands between 50 and 60 kDa, 80, and 95 kDa). See FIG. 9, Lane A. In infected IDE8 cells three bands were consistently present that were not detected in uninfected cultures. See FIG. 9 arrows. Of these, a doublet of approximately 28 and 31 kDa was also seen in infected, but not in uninfected, tick salivary glands, and the third band corresponded to the 80 kDa protein in infected bovine blood.

A western blot comparison of antigenic profile of *A. marginale* infected erythrocytes, tick, salivary glands, and tick cell culture is shown in FIG. 10. The results show that bands at 80 kDa and the doublet at 30 kDa are seen in infected erythrocytes, infected ticks and in *A. marginale* from tick cell culture. These results indicate *A. marginale* from tick cell culture expresses antigens that are present also in naturally infected ticks and cattle, and are recognized by cattle immunized against the blood stages of *A. marginale*.

EXAMPLE 5

Preparation of Antigen from *A. marginale* grown in *Ixodes Scapularis* Cell Culture Antigen from *A. marginale* grown in *Ixodes scapularis* cell culture IDE8 was prepared for use in formation of an immune response in vaccine preparation, and for diagnostic assays.

Infected monolayers were removed from flasks after 4 weeks and when more than 80% of the cells were infected. The culture material was centrifuged at 1000×g for 10 minutes. The L15 medium was removed and the cells were washed in 2 ml sterile PBS. The pelleted cells were ground in glass tissue grinder at room temperature for 30 seconds and then transferred to an eppendorf tube. The disrupted cells were then sonicated for 2 minutes and then frozen at −70° C. for 2–7 days. The antigenic preparation was then thawed and allowed to sit at room temperature for 60 minutes.

EXAMPLE 6

Growth of *Rickettsia rickettsii* in IDE8 Tick Cell Culture

IDE8 cell cultures were used to study the growth of spotted fever group of rickettsia through vector cells. For this purpose a non-virulent spotted fever rickettsia coded MOAa was used. MOAa was isolated from the lone star tick, *Amblyomma americanum* using tick cell culture. For comparison, *R. Rickettsii* strain Hlp-2 was included. Infectious inoculum was obtained from field collected *A. americanum* ticks that had been surface-sterilized by sequential washes in 1% Na-hypochlorite (bleach diluted 1:5 with sterile water), 0.5% benzalkonium chloride, and 70% ethanol, followed by three rinses in sterile water. Ticks were then cut open using a sterile scalpel blade, and the internal organs removed in toto and placed into IDE8 cultures. One to 5 ticks were used per each 5 ml IDE8 culture. Infectious inoculum could also consist of rickettsiae previously grown in IDE8 culture or grown in yolk sack culture. Usually, 1 to 2% of an infected culture was transferred to an uninfected culture. The medium consisted either of L15B supplemented as for tick cell propagation, or as for the propagation of *A. marginale* and *E. canis* outlined in Examples 2 and 7. Infected cultures were incubated at 34° C.

In tick cell culture, spotted fever rickettsiae expressed the major outer membrane protein rompB as determined by reactivity with a monoclonal antibody (data not shown). Antiserum from a rabbit immunized with virulent *R. rickettsii* strain "Sheila Smith" also specifically reacted with *R. rickettsii* grown in tick cell culture, further indicating continued expression of major rickettsial outer membrane proteins in this system. At early stages after infection (days 3 to 5 pi), few rickettsiae were found in infected cells, but from day 6 onward, the cells became heavily infected, and eventually lysed to release the parasites (data not shown). Double staining for f-actin (using rhodamine-labeled phalloidin) and rickettsiae revealed that in tick cells rickettsiae induce polymerization of actin on one pole of the rickettsial cell, causing them to move within and between tick cells (data not shown).

These results further support the claim that tick cell line IDE8 is broadly susceptible to many rickettsial organisms, namely spotted fever rickettsiae, Anaplasma, and Ehrlichia. This cell line is a suitable substrate for rickettsial growth, allowing the study of rickettsial biology within vector cells as well as the production of pathogens for their use as antigens for diagnostic purposes or in vaccines.

EXAMPLE 7

Propagation of *Ehrlichia canis* in IDE8 Tick Cell Culture

*Ehrlichia canis* is a rickettsial pathogen transmitted to dogs via the bite of the brown dog tick, *Rhipicephalus sanguineus*. Like its vector, *E. canis* is present in most parts of the world, but is a problem especially in warmer climates.

Cultured tick cells have been inoculated with white blood cells harvested from buffy coat of dogs infected with *E. canis*. Infected dog blood was obtained from Dr. Sidney Ewing, Oklahoma State University, Stillwater, Okla. Successful isolation of *E. canis* required the addition of 0.25% $NaHCO_3$ and 10 mM MOPS (an organic buffer) to tick cell culture medium (L-15B with 5% FBS, 10% TPB, 0.1% lipoprotein concentrate), and incubation of cultures in an atmosphere enriched with $CO_2$ and with reduced $O_2$ at 34° C. These conditions were achieved by placing the cultures, screw caps loose, into a candle jar overnight. Cultures were fed and examined weekly. Three to five weeks pi, infected cells were first seen in cell spreads stained with Giemsa's stain. Of several cell lines tested, including one from the vector, *R. sanguineus*, only line IDE8 from the black-legged tick, *Ixodes scapularis*, supported *E. canis* growth.

At that time, less than 1% of the cell population contain ehrlichiae within membrane-lined, parasitophorous vacuoles. Single organisms appear highly pleomorphic and number from a few to hundreds per endosome as seen by light and electron microscopy. Within about 7 weeks pi, the level of infection increases to about 20%, and the first passage can be made by adding one tenth of the infected cell layer to a new, established IDE8 culture. Subsequently, 80 to 90% of tick cells became infected and the rickettsiae are passaged 1 to 10 every 3 weeks. See FIG. 11, top panel. With continued passage, it is no longer necessary to use the candle jar, and *E. canis* is grown in tightly capped flasks at 34° C.

Oligonucleotide primers specific for *E. canis* (ECAN5-forward and ESPEC3-reverse, designed by Dr. George Murphy, Oklahoma State University; ECAN5 5' CAA TTA TTT ATA GCC TCT GGC TAT AGG A 3'; ESPEC3 5' TAT AGG TAC CGT CAT TAT CTT CCC TAT 3') confirmed the identity of the cultured rickettsiae when used in the polymerase chain reaction (PCR). See FIG. 12. DNA was amplified during 30 cycles of denaturing for 45 sec. at 94° C., annealing for 30 sec. at 55° C., and extension for 90 sec. at 72° C. A single final extension cycle at 72° C. for 10 min. concluded the program. For both templates, the expected size of the amplicon is ~400 bp.

An indirect immunofluorescent assay further indicated that *E. canis* grown in tick cells reacts specifically with antiserum from dogs experimentally infected with the rickettsiae. Cultures of *I. scapularis* tick cell line IDE8 in which over 50% of the cells were infected with *E. canis* were used for IFA. About 10,000 to 50,000 cells were spun onto microscope slides, the slides were air dried, and fixed twice in absolute methanol for at least 10 min. Slides were stored at −20° C. in a desiccator until use. Slides were thawed, overlayed with canine serum against *E. canis* usually diluted 1 to 10 to 1 to 1000, and incubated in a humid chamber for 30 min at 37° C. Slides were rinsed in sterile water, and immersed in phosphate buffered saline (PBS) pH 7.2 with 3% bovine serum albumin (BSA) for 10 min. Slides were rinsed in PBS, overlaid with anti-canine lgG labelled with fluorescein isothiocyanate (FITC) (usually diluted 10 fold in PBS with 3% BSA), and incubated for 30 min. at 37° C. in a humid chamber. Slides were rinsed in PBS, and coverslips mounted in PBS with 3% BSA and 10% glycerol. Slides were examined using a microscope equipped with a UV light source and epifluorescence illumination.

The results are shown in FIG. 11, panel B. Ehrlichial inclusions appear bright green against minimally staining tick host cells. To reduce non-specific staining, sera should be optimally diluted, and Evan's blue may be used as a counter stain.

These results show that *Ixodes scapularis* tick cell culture supports the growth of monocytic Ehrlichiae. This cell line is suitable for rickettsial growth for the production of pathogens for use as antigens or in vaccines.

EXAMPLE 8

Infectivity of *E. canis* Grown in *Ixodes scapularis* Tick Cell Culture

*Ehrlichia canis* grown in IDE8 tick cell culture is infectious and pathogenic for dogs. Two dogs were injected intravenously with the contents of one *E. canis* culture each. One dog received a culture, passaged once, in which 81% of the cells were infected as determined by evaluation of Giemsa-stained cell smears. The second dog received a culture, passaged three times, in which 64.3% of the cells were infected. Both dogs developed fever (≦104° F.) within 10 days post exposure, and morulae of *E. canis* were demonstrated in the blood thereafter. The dogs also experienced depression, inappetence, and pancytopenia, symptoms typical of canine ehrlichiosis. *Ehrlichia canis* was reisolated from the blood of both dogs into IDE8 cell culture.

A Walker Hound pup was exposed to adult *Rhipicephalus sanguineus* that had acquisition fed as nymphs on a dog previously infected with *E. canis* passaged in IDE8 cells. The ticks fed on the Walker Hound pup for about 12 days and then the ticks were removed. The pup's temperature was taken twice a day and blood films were made daily. About 7 to 10 days after tick removal, fever was detected. At about 10 days after tick removal, the first morula was observed in a blood monocyte. Platelet counts also decreased over this time period. The platelet count was initially $320\times10^3$ and at about 6 days after the ticks were removed the count was $78\times10^3$. At about 13 days after the ticks were removed the platelet count was at $40\times10^3$. The pup was showing definite symptoms of ehrlichiosis.

These results show that ticks that fed on a dog infected with *E. canis* passaged in IDE8 cells became infected and were able to transmit *E. canis* to another dog.

EXAMPLE 9

Western Blot Analysis of *E. canis* Grown in Tick Cells

Preparation of Antigen for Use in Immunoblots (Western Blots)

*Ehrlichia canis*-infected IDE8 cell cultures in which at least 50% of the cells were infected were preferably used. The cultures were resuspended and washed once in a balanced salt solution (BSS). Pelleted cells were transferred to microfuge tubes, and spun for 15 min. at 13,000 g. Pellets were mixed with extraction buffer (composed of 0.0625M Tris-HCl, 10% glycerol, 2% Na-dodecyl sulfate, 0.5% β-mercaptoethanol, and 0.00125% bromophenol blue), and boiled for 3 min. Extracts are clarified by centrifugation at 13,000 g for 15 min., and stored at −20° C. Extracts were diluted by mixing 2 μl of extract with 8 μl of extraction buffer, and loaded into the wells of a 12% polyacrylamide gel with a 4% stacking gel in Mini Protean (BioRad) apparatus. Samples were separated at 200 V for 50 min., and the proteins then transferred to a PVDP (Immobilon P. Millipore) membrane for 60 min. at 100 V. Membranes were washed 4 times in PBS pH 7.2 for 5 min. each time, blocked for 2 hours at room temperature using Blotto (5% non-fat dry milk in PBS), PBS with 3% BSA, or PBS with 10% horse serum. Blots were washed twice and then incubated at room temperature for 2 hours in primary antiserum diluted 1 to 100 to 1 to 1000, as appropriate. Blots were washed 4 times in PBS, and incubated in anti-canine lgG labelled with horse radish peroxidase at room temperature to 1 to 2 hours. Blots were washed in PBS 4 times and then developed with the TMB membrane system from Kirkegaard and Perry Laboratories as directed by the producer.

Figure 13:
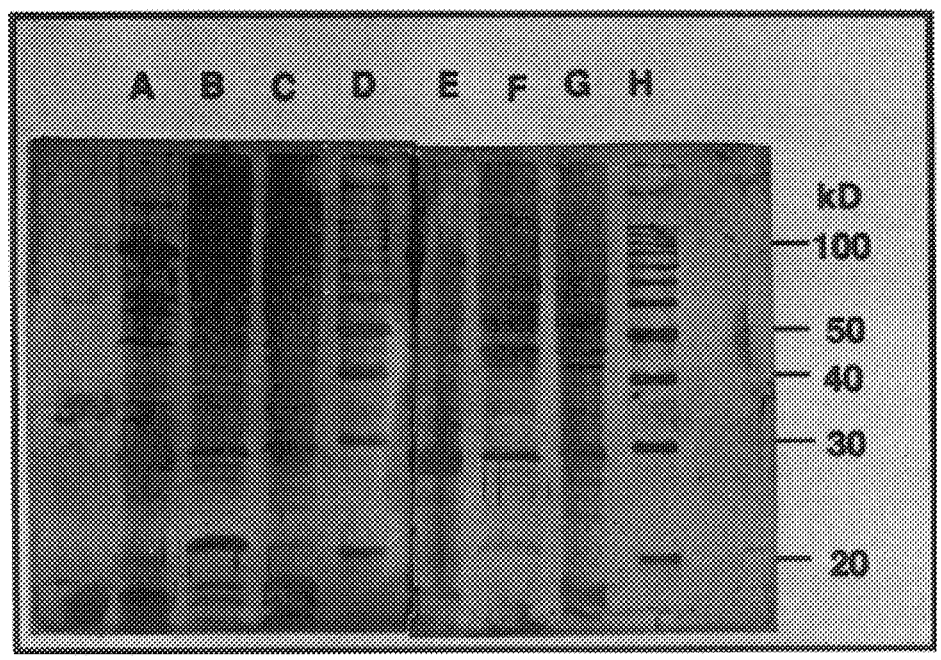
FIG. 13. Immunoblot of *E. canis* grown in IDE8 cultures (lanes B & F; first passage in vitro, two months post initiation of the culture) as compared with extract from buffy coat of an experimentally infected dog (lanes A & E), and uninfected IDE8 tick cells (lanes C & G). Molecular size markers are in lanes D & H, and selected sizes are indicated on the right margin. Bands specific for *E. canis* are indicated by arrows.

The results are shown in FIG. 13. Specific protein bands corresponding to bands also seen in blots made from infected dog white blood cells are detected at approximately 28 kD, 45 kD and 50 kD. These bands are absent in uninfected tick cell line IDE8 cell culture extracts.

---

What is claimed is:

1. A method for propagating rickettsiae in cell culture comprising:

incubating rickettsiae with tick cells derived from undifferentiated *Ixodes scapularis* cells under conditions of reduced oxygen and increased $CO_2$ in a culture medium supplemented with an organic buffer and suitable for growth of invertebrate cells to produce tick cells infected with rickettsiae, wherein said rickettsiae propagates in the incubating cells, and wherein said propagating rickettsiae is infective for cattle.

2. The method of claim 1, wherein the rickettsiae is *Anaplasma marginale*.

3. The method of claim 1, wherein the *Ixodes scapularis* tick cell culture has the identifying characteristics of tick cell line IDE8, ATCC No. CRL 11973.

4. The method of claim 1, wherein the *Ixodes scapularis* tick cell culture has the identifying characteristics of tick cell line ISE6, ATCC No. CRL 11974.

5. The method of claim 1, wherein the culture medium comprises: L-15B medium with 8 mM glucose, 0.1% bovine lipoprotein, and 3–5% bovine fetal calf serum.

6. A tick cell culture comprising undifferentiated *Ixodes scapularis* cells infected with propagating rickettsiae, which propagating rickettsiae is infective for cattle.

7. The infected tick cell culture of claim 6, wherein the rickettsiae is *Anaplasma marginale*.

8. A method for propagating *A. marginale* comprising:

incubating *A. marginale* with tick cells derived from undifferentiated *Ixodes scapularis* in a culture medium supplemented with an organic buffer and a source of $HCO_3^-$, the culture medium suitable for growth of invertebrate cells to produce tick cells infected with *A. marginale*, wherein said *A. marginale* propagates in the incubating cells, and wherein the propagated *A. marginale* is infective for cattle.

9. A method for propagating *A. marginale* comprising:

incubating *A. marginale* with tick cells derived from embryonic *Ixodes scapularis* cells in a culture medium supplemented with an organic buffer and a source of $HCO_3^-$, the culture medium suitable for growth of invertebrate cells to produce tick cells infected with *A. marginale*; wherein said *A. marginale* propagates in the incubating cells, and wherein the propagated *A. marginale* is infective in cattle.

10. A tick cell culture comprising embryonic tick cells infected with propagating rickettsiae, which propagating rickettsiae is infective in cattle.

11. A tick cell culture comprising embryonic *Ixodes scapularis* tick cells infected with propagating rickettsiae, which propagating rickettsiae is infective in cattle.

12. The infected cell culture of claim 11, wherein the rickettsiae is *Anaplasma marginale*.

13. The infected cell culture of claim 11, wherein the tick cells are grown in hollow tubes.

14. A method according to claim 1 wherein the rickettsia is *Ehrlichia canis*.

15. A method according to claim 1 wherein the rickettsia is *Rickettsia rickettsii*.

16. An infected tick cell culture according to claim 6 wherein the rickettsia is *Ehrlichia canis*.

17. An infected tick cell culture according to claim 6 wherein the rickettsia is *R. rickettsii*.

* * * * *

UNITED STATES PATENT AND TRADEMARK OFFICE
CERTIFICATE OF CORRECTION

PATENT NO. : 5,869,335
DATED : FEBRUARY 9, 1999
INVENTOR(S) : MUNDERLOH ET AL.

It is certified that error appears in the above-identified patent and that said Letters Patent is hereby corrected as shown below:

Title page, [73] Assignee: insert —Oklahoma State University, Stillwater, Okla.— on the line after "Minn."

Signed and Sealed this

Thirty-first Day of October, 2000

*Attest:*

Q. TODD DICKINSON

*Attesting Officer*  *Director of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

GTATGGCACG TAGTCTTGGG ATCA        24

( 2 ) INFORMATION FOR SEQ ID NO:2:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:2:

CAGCAGCAGC AAGACCTTCA        20